US012691203B2

(12) United States Patent
Weigel et al.

(10) Patent No.: US 12,691,203 B2
(45) Date of Patent: Jul. 28, 2026

(54) HIGH-POROSITY NANOFIBER NONWOVENS AS A SUPPORT STRUCTURE FOR STROMAL TISSUE

(71) Applicant: FRAUNHOFER-GESELLSCHAFT ZURFÖRDERUNG DER ANGEWANDTEN FORSCHUNG E.V., Munich (DE)

(72) Inventors: Tobias Weigel, Würzburg (DE); Florian Groeber-Becker, Würzburg (DE); Jan Hansmann, Würzburg (DE); Bastian Christ, Würzburg (DE); Jörn Probst, Würzburg (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 403 days.

(21) Appl. No.: 18/271,306

(22) PCT Filed: Oct. 26, 2021

(86) PCT No.: PCT/EP2021/079619
§ 371 (c)(1),
(2) Date: Jul. 7, 2023

(87) PCT Pub. No.: WO2022/148564
PCT Pub. Date: Jul. 14, 2022

(65) Prior Publication Data
US 2024/0082462 A1     Mar. 14, 2024

(30) Foreign Application Priority Data
Jan. 8, 2021    (DE) ..................... 10 2021 200 128.9
Mar. 1, 2021    (DE) ..................... 10 2021 201 935.8

(51) Int. Cl.
| | |
|---|---|
| A61L 27/56 | (2006.01) |
| B29C 64/118 | (2017.01) |
| B29K 31/00 | (2006.01) |
| B29K 77/00 | (2006.01) |
| B29K 105/04 | (2006.01) |
| B29L 31/00 | (2006.01) |
| B33Y 70/00 | (2020.01) |
| B33Y 80/00 | (2015.01) |
| C12N 5/071 | (2010.01) |
| C12N 5/077 | (2010.01) |
| D01F 1/10 | (2006.01) |
| D01F 6/16 | (2006.01) |
| D01F 6/60 | (2006.01) |
| D04H 1/4282 | (2012.01) |
| D04H 1/4334 | (2012.01) |
| D04H 1/4382 | (2012.01) |
| D04H 1/4391 | (2012.01) |
| D04H 1/56 | (2006.01) |
| D04H 1/728 | (2012.01) |

(52) U.S. Cl.
CPC ........... *A61L 27/56* (2013.01); *C12N 5/0629* (2013.01); *C12N 5/0653* (2013.01); *D01F 1/10* (2013.01); *D01F 6/16* (2013.01); *D01F 6/60* (2013.01); *D04H 1/4282* (2013.01); *D04H 1/4334* (2013.01); *D04H 1/43838* (2020.05); *D04H 1/43916* (2020.05); *D04H 1/56* (2013.01); *D04H 1/728* (2013.01); *A61L 2400/12* (2013.01); *A61L 2430/34* (2013.01); *B29C 64/118* (2017.08); *B29K 2031/04* (2013.01); *B29K 2077/00* (2013.01); *B29K 2105/04* (2013.01); *B29L 2031/7532* (2013.01); *B33Y 70/00* (2014.12); *B33Y 80/00* (2014.12); *D10B 2401/10* (2013.01); *D10B 2509/00* (2013.01)

(58) Field of Classification Search
CPC .. A61L 27/56; A61L 2400/12; A61L 2430/34; D04H 1/43838; D04H 1/43916; D04H 1/4282; D04H 1/4334; D04H 1/56; D04H 1/728; C12N 5/0629; C12N 5/0653; D01F 1/10; D01F 6/16; D01F 6/60; B33Y 70/00; B33Y 80/00; B29C 64/118; B29K 2077/00; B29K 2031/04; B29K 2105/04; B29K 2031/7532; D10B 2401/10; D10B 2509/00
See application file for complete search history.

(56) References Cited

FOREIGN PATENT DOCUMENTS

| | | |
|---|---|---|
| CN | 105727364 A | 7/2016 |
| WO | 2007125288 A1 | 11/2007 |
| WO | 2011143213 A1 | 11/2011 |
| WO | 2013023064 A2 | 2/2013 |
| WO | 2015079278 A1 | 6/2015 |
| WO | 2016105581 A1 | 6/2016 |

OTHER PUBLICATIONS

International Search Report on Written Opinion for PCT/EP2021/079619 dated Feb. 18, 2022, 17 pages.
(Continued)

*Primary Examiner* — Shirley V Gembeh
(74) *Attorney, Agent, or Firm* — Sheppard Mullin Richter & Hampton LLP

(57) ABSTRACT
The present invention relates to nanofiber nonwovens comprising a network of nanofibers, which are composed of at least one nanofiber material and which enclose pores, to methods for producing nanofiber nonwovens, to the use thereof as well as to artificial tissue comprising these nanofiber nonwovens and methods for producing these artificial tissues.

22 Claims, 11 Drawing Sheets

(56) References Cited

OTHER PUBLICATIONS

Figure 1:
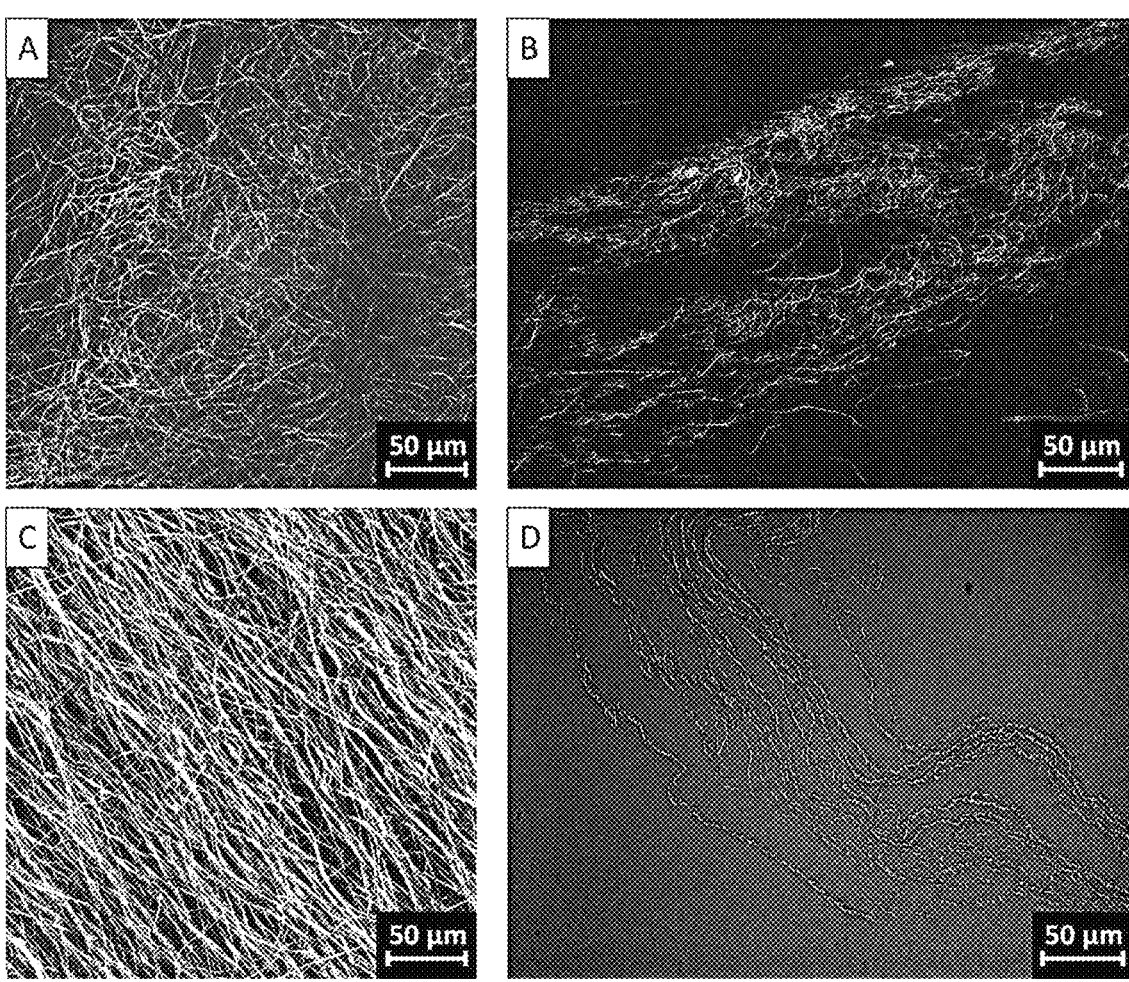

Kim, et al. Macroporous and nanofibrous hyaluronic acid/collagen hybrid scaffold fabricated by concurrent electrospinning and deposition/leaching of salt particles. Acta Biomaterialia. 2008; 4:1611-1619.

Semitela, et al. Electrospinning of bioactive polycaprolactone-gelatine nanofibres with increased pore size for cartilage tissue engineering applications. Journal of Biomaterials Applications. 2020; 35(4-5):417-484.

Weigel, et al. Generation of porous 3D-scaffolds based on electrospun nanofibers. Abstracts—Annual Meeting of the German Society for Biomaterials 2018—Braunschweig, Nov. 08-10. Biomed. Eng.—Biomed. Tech. 2019; 64(s1):p. 59-p. 62.

Wu, et al. Enhancing cell infiltration of electrospun fibrous scaffolds in tissue regeneration. Bioactive Materials. 2016; 1:56-64.

International Preliminary Report on Patentability for PCT/EP2021/079619 dated Jul. 20, 2023, 9 pages.

Figure 11

HIGH-POROSITY NANOFIBER NONWOVENS AS A SUPPORT STRUCTURE FOR STROMAL TISSUE

CROSS REFERENCE TO RELATED APPLICATIONS

This application is a U.S. National Stage Application under 35 U.S.C. 371 of International Application No. PCT/EP2021/079619, filed Oct. 26, 2021, which claims priority to German Patent Application 10 2021 200 128.9, filed on Jan. 8, 2021 and German Patent Application 10 2021 201 935.8, filed on Mar. 1, 2021. The contents of each of the which are hereby incorporated by reference in their entirety into the present disclosure.

The present invention relates to nanofiber nonwovens comprising a network of nanofibers, which are composed of at least one nanofiber material and which enclose pores, to methods for producing nanofiber nonwovens, to the use thereof as well as to artificial tissue comprising these nanofiber nonwovens and methods for producing these artificial tissues.

Research into the complex processes in biological tissues provides the basis for regenerative medicine. Historically, many of these experiments were carried out on animal models, for example to investigate healing processes, implants, drugs or the behaviour of tumours.

However, due to the differences between animals and humans, many processes cannot be represented correctly. Furthermore, attempts are currently being made to avoid animal experiments as far as possible according to the 3R principle (Refine, Reduce, Replace). Alternatives are in vitro generated tissue models, which represent a part of the tissue to be examined by using human cells.

In addition to cells, suitable carrier structures are also required for the construction of these tissues, which reproduce the basic structure and function of the extracellular tissue. These carrier structures have either a biological or synthetic origin. Biological carrier structures such as collagen gels or decellularised organs are often used with the aim of creating as physiological an environment as possible for the cells through the natural matrix proteins. The disadvantage, however, is that this involves material of animal origin. In these methods, both the killing of animals for organ removal and high quality variations between different batches or even within a batch are unavoidable.

Furthermore, it is not possible to produce a fully human tissue model. For this reason, developments have been underway for many years to produce cell carrier structures via synthetic routes. Carrier structures for soft tissue are mainly produced using additive manufacturing techniques, such as 3D printing of hydrogels or a variety of spinning processes.

The printing of hydrogels has the advantage that different cells and different tissues can be processed simultaneously in one construct. However, the disadvantage is, for example, the mechanical properties, which severely limit the applicability of the product. Today, spinning processes are capable of creating almost any conceivable fibre diameter. The challenge with the nanofibres relevant here, however, is the control of the fibre structure. For example, the orientation of the fibres can be easily adjusted, but the possibilities of porosity and especially the dimensions of the porosity for three-dimensional biological tissue applications are very limited. However, a suitable porosity is necessary for sufficient cell integration. If the porosity is too low, the cells can only penetrate the tissue in small numbers or not at all. When nanofibre nonwovens are produced via electrospinning, the meshes and pores are already so small that cells can either not colonize the tissue at all or only to a very limited extent.

Therefore, solutions are being sought to combine the excellent mechanical properties of nanofibres and high availability of various materials with possibilities for 3D structuring. The aim is to develop new methods for producing nanofibre-based 3D structures for the generation of 3D tissue models.

To increase porosity, soluble foreign objects (porogens) are usually immobilised between the fibres during the spinning process and then dissolved out again. The application of porogens with similar dimensions as the fibres of the support structure (500 nm to 10000 nm) leads to a loosening of the fibre structure and thereby mainly increases the mesh size of the fibre nonwoven.

The literature describes a considerable improvement for the migration of cells and thus also allows a three-dimensional cell culture, but too little space remains for the cells to build physiologically comparable biological tissue.

In WO2016/105581 A1, colonization occurs solely via the pores (interconnected), but these are hardly flexible and must be completely filled with cells (inhomogeneous distribution between cells and fibres). According to this disclosure, nanofibre nonwovens are milled to achieve short fibre pieces.

In WO 2007/125288 A1, the material used has dense pore walls. If one were to increase the porosity in this case, it works exclusively via the pore size. Increasing the pore size leads to less surface curvature and thus reduces the 3D character of the membrane for the cells. That is, larger pores provide a more 2D surface for the cells.

The technical problem underlying the present invention is to provide nanofibre nonwovens which do not have the aforementioned disadvantages of known cell support structures, in particular those which make it possible to produce artificial tissues more quickly which are more similar to a natural tissue than known artificial tissues, in particular with regard to the contact between the cells.

This technical problem is solved by a nanofibre nonwoven according to the teaching of the invention, in particular by a nanofibre nonwoven comprising a network of nanofibres composed of at least one nanofibre material and enclosing pores, wherein the porosity of the nanofibre nonwoven is 90.0 to 99.9 vol. %, in particular 98.5 to 99.9 vol. % (in each case based on the total volume of the nanofibre nonwoven).

The technical problem is also solved by a nanofibre nonwoven comprising a network of nanofibres composed of at least one nanofibre material and enclosing pores, produced by a first method comprising the method steps:

a) providing at least one nanofibre material and at least one porogen material suitable for formation of at least one porogen, b) electrospinning the at least one nanofibre material while introducing at least one porogen formed from the at least one porogen material having a diameter of 30 to 1000 μm, so that the volume ratio of porogen material to nanofibre material in the electrospun nanofibre nonwoven obtained after completion of this method step is 40 to 99 to 60 to 1 (in each case volume based on the total volume, i.e. fibres and porogens, of the nanofibre nonwoven), and c) obtaining a nanofibre nonwoven comprising at least one porogen.

In particular, the technical problem is solved by a first method for producing a nanofibre nonwoven comprising a network of nanofibres composed of at least one nanofibre material enclosing pores comprising the method steps:

a) providing at least one nanofibre material and at least one porogen material suitable for formation of at least one porogen, b) electrospinning said at least one nanofibre material while introducing at least one porogen formed from the at least one porogen material having a diameter of 30 to 1000 μm, so that the volume ratio of porogen material to nanofibre material in the electrospun nanofibre nonwoven obtained after completion of this method step is 40 to 99 to 60 to 1 (in each case volume based on the total volume, i.e. fibres and porogens, of the nanofibre nonwoven), and c) obtaining a nanofibre nonwoven comprising at least one porogen.

In a particularly preferred embodiment, the nanofibre nonwoven obtained according to a first method has a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven).

In a preferred embodiment, the volume ratio of porogen material to nanofibre material in the electrospun nanofibre nonwoven obtained after completion of method step b) according to the first method is 50 to 99 to 50 to 1, in particular 60 to 99 to 40 to 1, in particular 70 to 99 to 30 to 1, in particular 80 to 99 to 20 to 1 (in each case volume based on the total volume, i.e. fibres and porogens, of the nanofibre nonwoven).

The invention also relates to a second method for producing a nanofibre nonwoven according to the invention, comprising the following method steps:

a') providing at least one nanofibre material and at least one porogen material suitable for formation of at least one porogen, b') electrospinning the at least one nanofibre material while introducing at least one porogen formed from the at least one porogen material having a diameter of 30 to 1000 μm, so that the ratio of porogen material to nanofibre material in the electrospun nanofibre nonwoven obtained after completion of this method step is 0.07 to 99.997 to 99.93 to 0.003 (in each case by mass, based on the total mass, i.e. porogens and fibres, of the nanofibre nonwoven), and c') obtaining a nanofibre nonwoven comprising at least one porogen, in particular a nanofibre nonwoven having a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven).

In a particularly preferred embodiment, the nanofibre nonwoven obtained according to the second method has a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven).

In a preferred embodiment, the ratio of porogen material to nanofibre material in the electrospun nanofibre nonwoven obtained after completion of method step b') according to the second method is 0.5 to 99.99 to 99.5 to 0.01, in particular 1 to 99.95 to 99 to 0.05, in particular 10 to 99 to 90 to 1, in particular 20 to 99 to 80 to 1, in particular 40 to 99 to 60 to 1, in particular 80 to 99 to 20 to 1 (in each case by mass, based on the total mass, i.e. fibres and porogens, of the nanofibre nonwoven).

The invention also relates to nanofibre nonwovens produced by means of the aforementioned methods, in particular the first and second methods, comprising a network of nanofibres composed of at least one nanofibre material and enclosing pores.

Without being bound by theory, the nanofibre nonwoven according to the invention offers in particular the advantages that cells (for example fibroblasts) can tighten (contract) the high-porosity fibre nonwoven according to the invention, as is known for example from collagen gels, and that cells generate their own three-dimensional protein structure, in particular extracellular matrix, within the three-dimensional fibre structure. Depending on the cell type, this extracellular matrix is also specific as in natural tissue. For example, fibroblasts generate collagen I within the nonwoven (like connective tissue), mesenchymal stromal cells that are adipogenically differentiated generate collagen IV, and laminin and collagen IV are generated at the interface with the epithelium. The nanofibre nonwoven according to the invention provides a three-dimensional environment for cells introduced into it and the high flexibility of the nanofibre structure provided allows pore walls to grow together as the cell colonization process continues. The nanofibre nonwovens according to the invention are therefore characterised by the ability to allow good and rapid cell migration and colonization of the entire nanofibre nonwoven in a short time, for example within 2 weeks. The high-porosity nanofibre nonwoven according to the invention shows similar properties as decellularised biological tissue: if, according to the invention, there is sufficient liquid, in particular water, within the nanofibre nonwoven according to the invention, in particular the fibre structure, it is highly flexible and shows a gel-like character. If the water content is reduced, the mechanical properties are more comparable to fibres. By combining an electrospinning process with further additive manufacturing methods, structures on a higher micrometre scale made of (water-)soluble materials are incorporated between the nanofibres as porogen by a further method. This enables the standardisable production of synthetic support structures for 3D stromal tissues with very high and controllable porosities.

In a particularly preferred embodiment, the nanofibre nonwoven according to the invention is present together with a liquid, in particular in moist and/or liquid-impregnated form.

In a particularly preferred embodiment, at least one liquid is present in the nanofibre nonwoven according to the invention.

In a preferred embodiment, the at least one liquid present in a nanofibre nonwoven according to the invention is sorbed, in particular absorbed and/or adsorbed, in particular absorbed, in the nanofibre nonwoven. In a preferred embodiment, the liquid is sorbed in the nanofibre nonwoven according to the invention in a volume such that this volume corresponds to the volume of the maximum liquid capacity of the nanofibre nonwoven.

In a particularly preferred embodiment, in the nanofibre nonwoven according to the invention, preferably produced by a first and/or second method according to the invention, the volume of the at least one liquid is 90.0 to 99.9 vol. %, in particular 92.5 to 99.9 vol. %, in particular 95.0 to 99.9 vol. %, in particular 98.5% to 99.9 vol. % (in each case based on the total volume of the nanofibre nonwoven having at least one liquid).

In a particularly preferred embodiment, in the nanofibre nonwoven according to the invention, preferably produced by a first and/or second method according to the invention, the weight of the at least one liquid is 90.0 to 99.9 wt. %, in particular 92.5 to 99.9 wt. %, in particular 95.0 to 99.9 wt. %, in particular 98.5% to 99.9 wt. % (in each case based on the total weight of the nanofibre nonwoven having at least one liquid).

In a particularly preferred embodiment of the present invention, the dry substance content of the nanofibre nonwoven preferably having at least one liquid, preferably produced by a first and/or second method according to the invention, is 0.1 to 10.0 wt. %, in particular 0.1 to 7.5 wt. %, in particular 0.1 to 5.0 wt. %, in particular 0.1 to 1.5 wt. % (in each case based on the total weight of the nanofibre nonwoven having at least one liquid).

In a particularly preferred embodiment of the present invention, the dry substance content of the nanofibre nonwoven having at least one liquid according to the invention is the dry substance content of the nanofibres or the nanofibres and any porogens possibly present, in particular the nanofibres of the fibre nonwoven.

In a preferred embodiment, the invention relates to a nanofibre nonwoven, preferably produced by a first and/or second method according to the invention, wherein at least one liquid is present in the nanofibre nonwoven, in particular with a volume of 90.0 to 99.9 vol. %, in particular 92.5 to 99.9 vol. %, in particular 95.0 to 99.9 vol. %, in particular 98.5 to 99.9 vol. % of liquid (in each case based on the total volume of the nanofibre nonwoven), and wherein the dry substance content of the nanofibre nonwoven having at least one liquid according to the invention is 0.1 to 10.0 wt. %, in particular 0.1 to 7.5 wt. %, in particular 0.1 to 5.0 wt. %, in particular 0.1 to 1.5 wt. % (in each case based on the total weight of the nanofibre nonwoven having at least one liquid).

In a particularly preferred embodiment, the weight of the at least one liquid in the nanofibre nonwoven according to the invention, preferably produced by a first and/or second method according to the invention, is 90.0 to 99.9 wt. %, in particular 92.5 to 99.9 wt. %, in particular 95.0 to 99.9 wt. %, in particular 98.5% to 99.9 wt. % (in each case based on the total weight of the nanofibre nonwoven having at least one liquid) and the weight of the nanofibres of the nanofibre nonwoven is 0.1 to 10.0 wt. %, in particular 0.1 to 7.5 wt. %, in particular 0.1 to 5.0 wt. %, in particular 0.1 to 1.5 wt. % (in each case dry substance content of the nanofibre, in each case based on the total weight of the nanofibre nonwoven having at least one liquid), wherein preferably the weight of the at least one liquid adds up with the weight of the nanofibres to 100 wt. %.

In a preferred embodiment, the invention relates to a nanofibre nonwoven having a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven), at least one liquid being present in the nanofibre nonwoven, in particular with a volume of 90.0 to 99.9 vol. %, in particular 92.5 to 99.9 vol. %, in particular 95.0 to 99.9 vol. %, in particular 98.5 to 99.9 vol. % of liquid (in each case based on the total volume of the nanofibre nonwoven).

In a particularly preferred embodiment, in the nanofibre nonwoven of the invention having a porosity of 90.0 to 99.9 vol. %, the weight of the at least one liquid is 90.0 to 99.9 wt. %, in particular 92.5 to 99.9 wt. %, in particular 95.0 to 99.9 wt. %, in particular 98.5% to 99.9 wt. % (in each case based on the total weight of the nanofibre nonwoven having at least one liquid).

In a particularly preferred embodiment of the present invention, the dry substance content of the nanofibre nonwoven preferably having at least one liquid having a porosity of 90.0 to 99.9 wt. %, according to the invention, is 0.1 to 10.0 wt. %, in particular 0.1 to 7.5 wt. %, in particular 0.1 to 5.0 wt. %, in particular 0.1 to 1.5 wt. % (in each case based on the total weight of the nanofibre nonwoven having at least one liquid).

In a preferred embodiment, the invention relates to a nanofibre nonwoven having a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven), wherein at least one liquid is present in the nanofibre nonwoven, in particular with a volume of 90.0 to 99.9 vol. %, in particular 92.5 to 99.9 vol. %, in particular 95.0 to 99.9 vol. %, in particular 98.5 to 99.9 vol. % of liquid (in each case based on the total volume of the nanofibre nonwoven), and wherein the dry substance content of the nanofibre nonwoven having preferably at least one liquid according to the invention is 0.1 to 10.0 wt. %, in particular 0.1 to 7.5 wt. %, in particular 0.1 to 5.0 wt. %, in particular 0.1 to 1.5 wt. % (in each case based on the total weight of the nanofibre nonwoven having at least one liquid).

In a particularly preferred embodiment, the weight of the at least one liquid in the nanofibre nonwoven of the invention having a porosity of 90.0 to 99.9 vol. % is 90.0 to 99.9 wt. %, in particular 92.5 to 99.9 wt. %, in particular 95.0 to 99.9 wt. %, in particular 98.5% to 99.9 wt. % (in each case based on the total weight of the nanofibre nonwoven having at least one liquid) and the weight of the nanofibres of the nanofibre nonwoven being 0.1 to 10.0 wt.-%, in particular 0.1 to 7.5 wt. %, in particular 0.1 to 5.0 wt. %, in particular 0.1 to 1.5 wt. % (in each case dry substance content of the nanofibre, in each case based on the total weight of the nanofibre nonwoven having at least one liquid), wherein preferably the weight of the at least one liquid adds up with the weight of the nanofibres to 100 wt. %.

In a particularly preferred embodiment, the liquid present in a nanofibre nonwoven according to the invention is a liquid that does not attack, in particular does not degrade, structurally alter or destroy the nanofibres formed from the nanofibre material.

In a particularly preferred embodiment, the liquid present in a nanofibre nonwoven according to the invention is water.

In a particularly preferred embodiment, the liquid present in a nanofibre nonwoven according to the invention is an aqueous solution, in particular of one or more substances.

In a preferred embodiment, the pH of the aqueous solution which is present in a nanofibre nonwoven according to the invention is 1 to 13, in particular 1 to 11, in particular 2 to 11, in particular 3 to 11, in particular 5 to 9, preferably 6 to 8, in particular 7.

In a particularly preferred embodiment, when calcium carbonate has been used as the porogen material for producing the nanofibre nonwoven, the porogen is present in the nanofibre nonwoven and the nanofibre nonwoven is present in an aqueous solution, the pH of this aqueous solution is 4 to 5, in particular 4.5.

In a particularly preferred embodiment, when chitosan has been used as the porogen material for producing the nanofibre nonwoven, the porogen is present in the nanofibre nonwoven and the nanofibre nonwoven is present in an aqueous solution, the pH of this aqueous solution is 2 to 4, in particular 3.

In a particularly preferred embodiment, when zinc oxide has been used as the porogen material for producing the nanofibre nonwoven, the porogen is present in the nanofibre nonwoven and the nanofibre nonwoven is present in an aqueous solution, the pH of this aqueous solution is 1 to 3, in particular 2.

In a particularly preferred embodiment, when silica gel/ amorphous silica has been used as the porogen material for producing the nanofibre nonwoven, the porogen is present in the nanofibre nonwoven and the nanofibre nonwoven is present in an aqueous solution, the pH of this aqueous solution is 11 to 13, in particular 12.

In a preferred embodiment, the liquid present in a nanofibre nonwoven according to the invention is a buffered solution, in particular PBS (phosphate buffered saline), especially PBS+ (PBS with $Ca^{2+}$ and $Mg^{2+}$ ions). In particular, the buffered solution has as buffer system bicarbonate buffer, citrate buffer and/or acetate buffer.

In a particularly preferred embodiment, the liquid present in a nanofibre nonwoven according to the invention is a non-aqueous solution, in particular of one or more substances.

In a preferred embodiment, the liquid present in a nanofibre nonwoven according to the invention is ethanol.

In a preferred embodiment, the liquid present in a nanofibre nonwoven according to the invention is isopropanol.

In a preferred embodiment, the liquid present in a nanofibre nonwoven according to the invention is dimethyl sulphoxide.

In a particularly preferred embodiment, the liquid present in a nanofibre nonwoven according to the invention is a non-aqueous or aqueous solution of a substance or mixture of substances inert to the nanofibre material in a solvent, for example water.

In a particularly preferred embodiment, the pores in a nanofibre nonwoven according to the invention are distributed homogeneously or in a hierarchically structured manner.

In a particularly preferred embodiment, the nanofibre nonwoven, preferably produced by a first and/or second method according to the invention, additionally comprises porogens.

In a particularly preferred embodiment, the porogens are particulate or fibrous.

In a particularly preferred embodiment, the porogens have a diameter of 30 to 1000 μm, in particular 40 to 1000 μm, in particular 50 to 1000 μm, in particular 70 to 1000 μm, in particular 100 to 1000 μm, in particular 30 to 500 μm, in particular 40 to 500 μm, in particular 50 to 500 μm, in particular 70 to 500 μm, in particular 100 to 500 μm, in particular 30 to 250 μm, in particular 40 to 250 μm, in particular 50 to 250 μm, in particular 70 to 250 μm, in particular 100 to 250 μm, in particular 30 to 150 μm, in particular 40 to 150 μm, in particular 50 to 150 μm, in particular 70 to 150 μm, in particular 100 to 150 μm.

In a particularly preferred embodiment, the porogens have a diameter of 30 to 1000 μm, in particular 40 to 1000 μm, in particular 50 to 1000 μm, in particular 70 to 1000 μm, in particular 100 to 1000 μm, in particular 30 to 500 μm, in particular 40 to 500 μm, in particular 50 to 500 μm, in particular 70 to 500 μm, in particular 100 to 500 μm, in particular 30 to 250 μm, in particular 40 to 250 μm, in particular 50 to 250 μm, in particular 70 to 250 μm, in particular 100 to 250 μm, in particular 30 to 150 μm, in particular 40 to 150 μm, in particular 50 to 150 μm, in particular 70 to 150 μm, in particular 100 to 150 μm, wherein at least 70%, in particular at least 80%, in particular at least 90%, in particular at least 95%, in particular at least 99%, in particular 100%, of the porogens have a diameter of at least 30 μm, in particular at least 40 μm, in particular at least 50 μm, in particular at least 70 μm, in particular at least 100 μm.

In a particularly preferred embodiment, at least 70%, in particular at least 80%, in particular at least 90%, in particular at least 95%, in particular at least 99%, in particular 100%, of the porogens have a diameter of 30 to 1000 μm, in particular 40 to 1000 μm, in particular 50 to 1000 μm, in particular 70 to 1000 μm, in particular 100 to 1000 μm, in particular 30 to 500 μm, in particular 40 to 500 μm, in particular 50 to 500 μm, in particular 70 to 500 μm, in particular 100 to 500 μm, in particular 30 to 250 μm, in particular 40 to 250 μm, in particular 50 to 250 μm, in particular 70 to 250 μm, in particular 100 to 250 μm, in particular 30 to 150 μm, in particular 40 to 150 μm, in particular 50 to 150 μm, in particular 70 to 150 μm, in particular 100 to 150 μm.

In a particularly preferred embodiment of the present invention, at least one liquid and porogens are present in the nanofibre nonwoven according to the invention.

In a particularly preferred embodiment of the present invention, porogens are present in the nanofibre nonwoven according to the invention, in particular produced by a first and/or second method according to the invention, wherein the total weight of the porogens is 0.07 to 99.997 wt. %, in particular 10.0 to 99.99 wt. %, in particular 50.0 to 99.95 wt. %, in particular 80.0 to 99.95 wt. % (in each case based on the total weight of the nanofibre nonwoven).

In a preferred embodiment, the invention relates to a nanofibre nonwoven, preferably produced by a first and/or second method according to the invention, wherein porogens are present in the nanofibre nonwoven, in particular with a volume of 40.0 to 99.9 vol. %, in particular 50.0 to 99.9 vol. %, in particular 60.0 to 99.9 vol. %, in particular 70.0 to 99.9 vol. %, in particular 80.0 to 99.9 vol. %, in particular 90.0 to 99.9 vol. %, in particular 40.0 to 95.0 vol. %, in particular 50.0 to 95.0 vol. %, in particular 60.0 to 95.0 vol. %, in particular 70.0 to 95.0 vol. %, in particular 80.0 to 95.0 vol. %, in particular 90.0 to 95.0 vol. %, in particular 92.5 to 95.0 vol. %, of porogens (in each case based on the total volume of the nanofibre nonwoven).

In a particularly preferred embodiment of the present invention, in the nanofibre nonwoven according to the invention with a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven) porogens being present, wherein the total volume of the porogens is 40.0 to 95.0 vol. %, in particular 50.0 to 95.0 vol. %, in particular 60.0 to 95.0 vol. %, in particular 70.0 to 95.0 vol. %, in particular 80.0 to 95.0 vol. %, in particular 90.0 to 95.0 vol. %, in particular 40.0 to 90.0%, in particular 50.0 to 90.0 vol. %, in particular 60.0 to 90.0 vol. %, in particular 70.0 to 90.0 vol. %, in particular 80.0 to 90.0 vol. % (in each case based on the total volume of the nanofibre nonwoven).

In a particularly preferred embodiment of the present invention, the nanofibre nonwoven according to the invention with a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven), porogens being present, wherein the total weight of the porogens is 0.07 to 99.997 wt. %, in particular 10.0 to 99.99 wt. %, in particular 50.0 to 99.95 wt. %, in particular 80.0 to 99.95 wt. % (in each case based on the total weight of the nanofibre nonwoven).

In a preferred embodiment, the invention relates to a nanofibre nonwoven, wherein at least one liquid and porogens are present in the nanofibre nonwoven, in particular with a volume of 40.0 to 99.9 vol. %, in particular 50.0 to 99.9 vol. %, in particular 60.0 to 99.9 vol. %, in particular 70.0 to 99.9 vol. %, in particular 90.0 to 99.9 vol. %, in particular 40.0 to 95.0 vol. %, in particular 50.0 to 95.0 vol. %, in particular 60.0 to 95.0 vol. %, in particular 70.0 to 95.0 vol. %, in particular 80.0 to 95.0 vol. %, in particular 90.0 to 95.0 vol. %, in particular 92.5 to 95.0 vol. %, of porogens (in each case based on the total volume of the nanofibre nonwoven).

In a particularly preferred embodiment of the present invention, porogens and at least one liquid are present in the nanofibre nonwoven according to the invention, preferably produced by a first and/or second method according to the invention, wherein the total volume of the at least one liquid and the porogens is 90.0 to 99.9 vol. %, in particular 92.5 to 99.9 vol. %, in particular 95.0 to 99.9 vol. %, in particular 98.5% to 99.9 vol. % (in each case based on the total volume of the nanofibre nonwoven).

In a particularly preferred embodiment of the present invention, porogens and at least one liquid are present in the nanofibre nonwoven according to the invention, preferably produced by a first and/or second method according to the invention, wherein the total weight of the at least one liquid and the porogens is 90.00 to 99.99 wt. %, in particular 92.50 to 99.99 wt. %, in particular 95.00 to 99.99 wt. %, in particular 98.50% to 99.99 wt. % (in each case based on the total weight of the nanofibre nonwoven).

In a preferred embodiment, the invention relates to a nanofibre nonwoven, preferably produced by a first and/or second method according to the invention, wherein in the nanofibre nonwoven at least one liquid and porogens, in particular with a volume of 90.0 to 99.9 vol. %, in particular 92.5 to 99.9 vol. %, in particular 95.0 to 99.9 vol. %, in particular 98.5 to 99.9 vol. % of porogens and at least one liquid (in each case based on the total volume of the nanofibre nonwoven) are present and wherein the dry substance content of the nanofibre nonwoven is 0.1 to 10.0 wt. %, in particular 0.1 to 7.5 wt. %, in particular 0.1 to 5.0 wt. %, in particular 0.1 to 1.5 wt. % (in each case based on the total weight of the nanofibre nonwoven having at least one liquid).

In a particularly preferred embodiment of the present invention, the nanofibre nonwoven according to the invention with a porosity of 90.0 to 99.9 vol. %, in particular 92.5 to 99.9 vol. %, in particularly 95.0 to 99.9 vol. %, in particular 98.5 to 99.9 vol. % (in each case based on the total volume of the nanofibre nonwoven) porogens and at least one liquid being present, wherein the total volume of the liquid and porogens is 90.0 to 99.9 vol. %, in particular 92.5 to 99.9 vol. %, in particular 95.0 to 99.9 vol. %, in particular 98.5% to 99.9 vol. % (in each case based on the total volume of the nanofibre nonwoven).

In a particularly preferred embodiment of the present invention, the nanofibre nonwoven according to the invention with a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven) porogens and at least one liquid being present, wherein the total weight of the at least one liquid and porogens is 90.00 to 99.99 wt. %, in particular 92.50 to 99.99 wt. %, in particular 95.00 to 99.99 wt. %, in particular 98.50% to 99.99 wt. % (in each case based on the total weight of the nanofibre nonwoven).

In a preferred embodiment, the invention relates to a nanofibre nonwoven having a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven), wherein in the nanofibre nonwoven at least one liquid and porogens, in particular having a volume of 90.0 to 99.9 vol. %, in particular 92.5 to 99.9 vol. %, in particular 95.0 to 99.9 vol. %, in particular 98.5 to 99.9 vol. %, of porogens and liquid (in each case based on the total volume of the nanofibre nonwoven), and wherein the dry substance content of the nanofibre nonwoven is 0.1 to 10.0 wt. %, in particular 0.1 to 7.5 wt. %, in particular 0.1 to 5.0 wt. %, in particular 0.1 to 1.5 wt. % (in each case based on the total weight of the nanofibre nonwoven having at least one liquid).

In a particularly preferred embodiment, the nanofibre nonwoven, preferably produced by a first and/or second method according to the invention, comprises no porogens.

In a particularly preferred embodiment of the present invention, no porogens are present in the nanofibre nonwoven having a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven).

Preferably, the nanofibres have a diameter of 100 to 1000 nm, in particular 200 to 1000 nm, in particular 300 to 1000 nm, in particular 100 to 900 nm, in particular 200 to 900 nm, in particular 300 to 900 nm, in particular 100 to 800 nm, in particular 200 to 800 nm, in particular 300 to 800 nm, in particular 100 to 700 nm, in particular 200 to 700 nm, in particular 300 to 700 nm.

In a particularly preferred embodiment, the nanofibres of the nanofibre nonwoven are present in a nanofibre nonwoven according to the invention in the form of nanofibre layers.

In a particularly preferred embodiment, the network of nanofibres is a flexible network, in particular constructed from nanofibre layers.

In the context of the present invention, a "fibre layer" or "nanofibre layer" is understood to mean a layer of nanofibres arranged above and/or next to one another, in particular above one another, in particular individual nanofibre layers are separated from one another by the pores. Preferably, the nanofibres and nanofibre layers of the nanofibre nonwoven according to the invention are obtained by a method for producing a nanofibre nonwoven according to the invention, in particular its method step b) or b').

In a preferred embodiment, the fibre layers comprise, in particular consist of, 1 to 25 fibres, in particular 3 to 20 fibres, in particular 3 to 15 fibres, in particular 3 to 10 fibres, which are arranged above and/or next to one another, in particular above one another.

In a particularly preferred embodiment, the fibre layers comprise, in particular consist of, 1 to 25 fibres, in particular 3 to 20 fibres, in particular 3 to 15 fibres, in particular 3 to 10 fibres, which are arranged above and/or next to one another, in particular above one another, in each case based on a depth of the nanofibre nonwoven of 10 μm.

In a preferred embodiment, the fibres in the fibre layer have no permanent contact and are freely movable in all spatial directions.

The structure of a nanofibre nonwoven according to the invention preferably comprises at least two, preferably several individual nanofibre layers, which are preferably separated by the pores, preferably-generated by the removal of porogens preferably provided according to the invention. Depending on the production preferred according to the invention, these pores may be closed off by the nanofibre layers or may have a very long to infinite laminar character.

Within the individual nanofibre layers, according to the invention, the free spaces, perpendicular to the main expansion surface of the nanofibre nonwoven, between the nano-fibres are referred to as meshes.

In the context of the present invention, a "mesh" is understood to mean the space between the individual nano-fibres of a nanofibre nonwoven according to the invention, in particular the space which has not been created by removing a porogen provided according to the invention during or after the production of the nanofibre nonwoven. In particular, meshes are understood to be the free spaces which are perpendicular to the main expansion surface of the nanofibre nonwoven.

A mesh is formed by superimposing and/or juxtaposing individual nanofibres to form nanofibre layers. The mesh that is formed is determined by the thickness of the indi-vidual nanofibre layers via the passage area that is formed.

The meshes are important in that cells can pass through them.

Therefore, according to the invention, the size of the "mesh" is also specified as an area (passage area with defined mesh size).

The mesh size depends, among other things, on the number of nanofibre layers on top of each other. The more nanofibre layers there are on top of each other, the smaller the mesh, i.e. the mesh size, and the more tightly the nanofibres are jammed together, both of which reduce the accessibility for cells.

In a preferred embodiment, the nanofibre nonwoven has meshes with a maximum mesh size of 200 $\mu m^2$, in particular a maximum of 150 $\mu m^2$, in particular a maximum of 100 $\mu m^2$, in particular a maximum of 50 $\mu m^2$.

In a preferred embodiment, the mesh size is 10 to 200 $\mu m^2$, in particular 20 to 200 $\mu m^2$, in particular 50 to 200 $\mu m^2$, in particular 100 to 200 $\mu m^2$, in particular 150 to 200 $\mu m^2$, in particular 10 to 150 $\mu m^2$, in particular 20 to 150 $\mu m^2$, in particular 50 to 150 $\mu m^2$, in particular 100 to 150 $\mu m^2$, in particular 10 to 100 $\mu m^2$, in particular 20 to 100 $\mu m^2$, in particular 50 to 100 $\mu m^2$, in particular 10 to 50 $\mu m^2$, in particular 20 to 50 $\mu m^2$. In particular, the nanofibre nonwo-ven has meshes with a mesh size corresponding to this paragraph.

In a preferred embodiment, the nanofibre nonwoven has 3000 to 8000 meshes per $mm^2$, in particular 3500 to 7000 meshes per $mm^2$, in particular 3000 to 6000 meshes per $mm^2$, in particular 3100 to 5000 meshes per $mm^2$, in particular 3200 to 4800 meshes per $mm^2$, in particular 3500 to 4500 meshes per $mm^2$. In a particularly preferred embodi-ment, only meshes with a minimum mesh size of 0.5 $\mu m^2$ are determined when determining the meshes per $mm^2$.

In the context of the present invention, a "pore" is understood to mean a space enclosed by nanofibre layers which can be filled by porogens, cells or fluids, i.e. liquids or gases. Preferably, the pores spatially separate the indi-vidual nanofibre layers from each other.

A pore extends within the nanofibre nonwoven according to the invention in the x-y-z direction (width, depth, height of the pore), wherein the depth and width of the pores describe the surface expansion directions of the nanofibre nonwoven. The height of the pores extends perpendicularly to the surface expansion directions of the nanofibre nonwo-ven and is preferably arranged in the direction of the height of the nanofibre nonwoven (also referred to as the thickness of the nanofibre nonwoven according to the invention). The width and depth of the pores are respectively defined as directions parallel to the directions of expansion of the nanofibre nonwoven.

The purpose of the pores is also to separate the individual nanofibre layers from each other and thus stabilise the preferred high mesh size. If the pore structure collapses, the mesh size also decreases, destroying the three-dimensional-ity for cell colonisation. The width, depth and height of the pores are determined in particular without mechanical stress on the nanofibre nonwoven, in particular without clamping the nanofibre nonwoven in a device, preferably directly after removal of the porogen.

The height of the pores preferably corresponds to the diameter of the porogen and can, if necessary, change due to the movement of the, in particular flexible, nanofibre non-woven according to the invention (compression of the nanofibre nonwoven leads to an increase in the height of the pores; tensile stress on the nanofibre nonwoven leads to a reduction in the height of the pores).

The width or depth of the pores is preferably many times greater than the diameter of the porogen, since the nanofi-bres are deposited over the porogen in a stretched state during the spinning process. The higher the rotation speed of the target (fibre orientation), the further the nanofibres are stretched and the wider the pore becomes. In extreme cases, the next porogen is close enough that the nanofibres no longer touch the lower nanofibre layer and are stretched over the porogen. This results in a lamellar structure, making the pores infinite in at least one direction of expansion (for example, width).

Preferably, this infinite pore expansion is only present in one direction. The other expansion direction (for example depth) preferably remains limited. This limitation depends on the porogen size.

Preferred is a maximum pore width corresponding to 3 to 5 times the pore diameter.

Preferred is a maximum pore depth corresponding to 3 to 5 times the pore diameter.

Very large porogens preferably lead to a layered structure, since here the nanofibres are stretched over the porogens in each direction of expansion. This layered structure prefer-ably leads to an effective separation of the individual nano-fibre layers and does not impair the colonization with cells.

Preferred embodiments represent pores having a width and/or depth of 150 to 250 $\mu m$, in particular when the porogens used to produce the nanofibre nonwoven according to the invention have diameters of 20 to 100 $\mu m$, in particular 50 $\mu m$.

Preferred embodiments are pores having a width and/or depth of 1500 to 2500 $\mu m$, in particular when the porogens used for producing the nanofibre nonwovens according to the invention have diameters of 200 to 1000 $\mu m$, in particu-lar 500 $\mu m$.

In a preferred embodiment, the pore depth is 50 to 5000 $\mu m$, in particular 100 to 5000 $\mu m$, in particular 50 to 2000 $\mu m$, in particular 100 to 2000 $\mu m$, in particular 50 to 1000 $\mu m$, in particular 100 to 1000 $\mu m$, in particular 50 to 500 $\mu m$, in particular 100 to 500 $\mu m$.

In a preferred embodiment, the pore width is 50 to 5000 $\mu m$, in particular 100 to 5000 $\mu m$, in particular 50 to 2000 $\mu m$, in particular 100 to 2000 $\mu m$, in particular 50 to 1000 $\mu m$, in particular 100 to 1000 $\mu m$, in particular 50 to 500 $\mu m$, in particular 100 to 500 $\mu m$.

In a preferred embodiment, the pore height is 20 to 1000 $\mu m$, in particular 50 to 1000 $\mu m$, in particular 20 to 500 $\mu m$, in particular 50 to 500 $\mu m$.

In the context of the present invention, "porosity" is understood to mean the percentage of the total volume of the nanofibre nonwoven formed by the volume of the pores and the meshes. The volumes of the pores may be filled with liquid and/or porogens.

In a preferred manner, the porosity of the nanofibre nonwoven provided according to the invention is present when the nanofibre nonwoven is present in liquid, in particular with a volume of 90.0 to 99.9 vol. %, in particular 92.5 to 99.9 vol. %, in particular 98.5 to 99.9 vol. % of liquid (in each case based on the total volume of the nanofibre nonwoven), in particular is present without mechanical stress, in particular tensile or compressive stress.

In a preferred manner, the porosity of the nanofibre nonwoven provided according to the invention is present when the nanofibre nonwoven is present in liquid and with porogens, in particular with a volume of 90.0 to 99.9 vol. %, in particular 92.5 to 99.9 vol. %, in particular 98.5 to 99.9 vol. % of porogens and liquid (in each case based on the total volume of the nanofibre nonwoven), in particular without mechanical stress, in particular tensile or compressive stress.

In particular, the porosity in vol. % is determined according to formula (A), in particular without subjecting the nanofibre nonwoven to a mechanical stress, in particular tensile or compressive stress, during the porosity determination.

$$\text{Porosity } P = (V_{Total} - V_{Fibres})/V_{Total} \times 100, \qquad \text{Formula (A):}$$

wherein $V_{Total}$ is the volume of the entire nanofibre nonwoven and $V_{Fibres}$ is the volume of the total fibres present in the nanofibre nonwoven.

In particular, the porosity in vol. % is determined according to formula (B), in particular without subjecting the nanofibre nonwoven to a mechanical stress, in particular tensile or compressive stress during the porosity determination.

$$\text{Porosity } P = (\text{Thickness}_{porous\ nonwoven} \times A_{macroscopic} - m_{Fibre}/\text{density}_{fibre\ material})/(\text{Thickness}_{porous\ nonwoven} \times A_{macroscopic}) \times 100. \qquad \text{Formula (B):}$$

Particularly preferably, the porosity of a nanofibre nonwoven is therefore determined according to formula (B) by determining the thickness (also referred to as the height of the nanofibre nonwoven according to the invention) of a piece of the porous nanofibre nonwoven and measuring the dry mass (m), of the fibres of the piece of the nanofibre nonwoven. Subsequently, by including the macroscopically determined surface area (A) of the piece of the nanofibre nonwoven and the theoretical density of the nanofibre material, in particular polymer, the porosity can be calculated in vol. %, based on the total volume of the nanofibre nonwoven.

In the context of the present invention, the macroscopically determined "surface area (A)" of the piece of the nanofibre nonwoven is particularly understood to mean the surface area formed by the width and depth (i.e. the surface expansion directions) of the nanofibre nonwoven, particularly of a piece of the nanofibre nonwoven.

In particular, the porosity is determined in vol. % according to the determination method according to example 2a, in particular without subjecting the nanofibre nonwoven to a mechanical stress, in particular tensile or compressive stress, during the porosity determination.

In particular, the porosity of a nanofibre nonwoven is determined according to the invention by means of confocal reflection microscopy in an aqueous solution, in particular water, without porogen, in particular wherein the nanofibre nonwoven is without mechanical stress, in particular tensile or compressive stress, apart from the hydrostatic pressure of the aqueous solution and the atmospheric pressure. Preferably, the porosity is determined according to the determination method of example 2b, in particular without subjecting the nanofibre nonwoven to a mechanical stress, in particular tensile or compressive stress, during the porosity determination.

In a preferred embodiment of the determination of the porosity of a nanofibre nonwoven by confocal reflection microscopy, any porogens present are removed from the piece of the nanofibre nonwoven and the nanofibre nonwoven is completely covered with the aqueous solution, in particular water. Subsequently, optical sectional images of a defined volume of the nanofibre nonwoven are created with the confocal reflection microscope. Using these optical sectional images, the volume of the nanofibres ($V_{fibres}$), in particular the volume occupied by the nanofibres in the optical sectional images, and the volume of all free spaces between the nanofibres ($V_{free\ space}$) are determined. The porosity can then be calculated using the following formula (C):

$$\text{Porosity } P = V_{free\ space}/(V_{free\ space} + V_{Fibres}) \times 100. \qquad \text{Formula (C):}$$

In particular, the determination of the porosity is carried out with a confocal microscope, in particular by means of confocal reflection microscopy, at a temperature of 20 to 25° C., in particular 20° C. In particular, the aqueous solution in which the nanofibre nonwoven is present is tempered during the determination of the porosity, in particular to 20 to 25° C., in particular 20° C.

In a particularly preferred embodiment of the present invention, the porosity of the nanofibre nonwoven according to the invention is determined immediately after removal of the porogen used for its production according to the invention, in particular of all the porogens, in particular within 3 days, in particular within 1 day, in particular within 8 hours, in particular within 7 hours, in particular within 5 hours, preferably within 30 min and particularly preferably within 10 min after removal of the porogen.

In particular, the porosity of the nanofibre nonwoven according to the invention is determined immediately after removal of the porogen from the nanofibre nonwoven, without the nanofibre nonwoven being mechanically stressed during the determination, for example by clamping in a device, in particular for example a cell culture device. The porosity determined according to the invention is therefore a porosity that has preferably been determined immediately after removal of the porogen on a nanofibre nonwoven that has not been subjected to mechanical tension or compression or other mechanical stress, in particular in the liquid, in particular in water.

Preferably, the size of the mesh is given in the form of a mesh size in the nanofibre nonwoven according to the invention without porogen, in particular determined by means of microscopy methods. The mesh size is therefore a two-dimensional variable.

The measurement of the mesh size is carried out after the porogen has been dissolved out in liquid, in particular in water, in particular without mechanical stress of the nanofibre nonwoven, in particular without clamping of the nanofibre nonwoven, so as not to influence the structure as far as possible. The most suitable way to do this is to use laser scanning microscopy (LSM) or the similar method convocal reflection microscopy. From the resulting 3D image, the individual images of a nanofibre layer were then superimposed to form a 2D image. The area of the spaces between the nanofibres is then determined.

In the context of the present invention, a "flexible network" is understood to mean a network of nanofibres in which nanofibres and nanofibre layers formed from these nanofibres are movable. In particular, flexibility means that cells are able to move individual nanofibres, but also entire nanofibre layers, in particular to pull them together.

In a preferred embodiment, the nanofibres in the network of nanofibres are oriented along an extension direction of the nanofibre nonwoven.

In a preferred embodiment, the nanofibres in the network of nanofibres are randomly oriented, that is in particular not oriented along an extension direction of the nanofibre nonwoven.

In a preferred embodiment, the nanofibre material is selected from the group consisting of synthetic polymers, in particular modified natural polymers, natural polymers, for example chitosan, hydroxyalkylcellulose, amorphous metal oxides and their hybrid (organic/inorganic) modifications, hybrid materials of synthetic and natural materials, ceramics, bioglasses, metals, carbon and combinations thereof.

In a particular embodiment of the invention, the synthetic polymer as nanofibre material is selected from the group consisting of polyester, in particular PCL, PLA, PGA, PET, PC and their copolymers, polyamides, in particular nylon and perlon types, polyurethanes, polyacrylonitrile, polystyrene, polyethylene/polypropylene, polyvinyl chloride, polyketones, in particular PEK, PEEK, polyethylene glycols, polyvinyl alcohols, polyoxazolines, polypeptoids, polypeptides, in particular polylysine, and combinations thereof.

In a particular embodiment of the invention, the natural polymer as nanofibre material is selected from the group consisting of polysaccharides, in particular chitosans, cellulose derivatives, in particular hydroxyalkylcelluloses, alginates, lignins, hyaluronic acid, heparin, structural proteins, in particular collagens, fibrin, elastin, laminins, vitronectin, fibronectin, plant proteins such as zein, other proteins or peptides, in particular enzymes, signal proteins, growth factors, nucleic acids, in particular DNA, RNA, and combinations thereof.

In a particular embodiment of the invention, the hybrid materials as nanofibre materials are Ormocer®, titanium oxo-carboxo clusters and/or silica and silica gel materials.

In a particular embodiment of the invention, ceramics as nanofibre material are present as fibres or particulate in polymer matrix.

In a particular embodiment of the invention, bioglasses as nanofibre material are present as fibres or particulate in polymer matrix.

In a particular embodiment of the invention, metals as nanofibre material are present as particulate in polymer matrix.

In a particular embodiment of the invention, carbon as nanofibre material is present as a fibre or particulate in polymer matrix.

In a particularly preferred embodiment, the nanofibre material has a density of 0.5 to 5 g/cm$^3$, in particular 1 to 5 g/cm$^3$, in particular 1 to 2.5 g/cm$^3$, in particular 1 to 2 g/cm$^3$.

In a preferred embodiment, the nanofibre nonwoven has a thickness of 50 to 5000 μm, in particular 100 to 5000 μm, in particular 50 to 4000 μm, in particular 100 to 4000 μm, in particular 50 to 3000 μm, in particular 100 to 3000 μm, in particular 50 to 2000 μm, in particular 100 to 2000 μm, in particular 50 to 1000 μm, in particular 100 to 1000 μm, in particular 50 to 500 μm, in particular 100 to 500 μm.

In a preferred embodiment, the porogen comprises, in particular consists of, at least one porogen material selected from the group consisting of water-soluble porogen material, in particular salts, polymers and/or saccharides, ethanol-soluble porogen material, pH-sensitive porogen material, enzymatically degradable porogen material, porogens degradable and/or absorbable in physiological solutions, and combinations thereof.

In a particular embodiment of the invention, the water-soluble porogen material is selected from the group consisting of water-soluble salts, in particular NaCl, NaCO$_3$, water-soluble polymers, in particular PEG/PEO, PVA, PVP, water-soluble saccharides or polysaccharides, in particular sucrose or other sugars, dextran, hybrid materials, in particular titanium-oxo-carboxo clusters, and combinations thereof.

In a particularly preferred embodiment, the porogen material is selected from the group consisting of NaCl, NaCO$_3$, PEG/PEO, sugar, CaCO$_3$, chitosan, zinc oxide and silica gel/amorphous silica.

In a particularly preferred embodiment, the porogen material is selected from the group consisting of NaCl, NaCO$_3$, PEG/PEO and sugar.

In a particularly preferred embodiment, the porogen material is selected from the group consisting of CaCO$_3$, chitosan, zinc oxide and silica gel/amorphous silica.

In a particularly preferred embodiment of the present invention, the porogen material is particulate.

In a particular embodiment of the invention, the ethanol-soluble porogen material is a polymer, in particular PVA.

In a particularly preferred embodiment, the porogen material has a density of 0.01 to 20 g/cm$^3$, in particular 0.5 to 20 g/cm$^3$, in particular 1 to 20 g/cm$^3$, in particular 5 to 20 g/cm$^3$, in particular 0.5 to 15 g/cm$^3$, in particular 1 to 10 g/cm$^3$, in particular 2 to 8 g/cm$^3$, in particular 1 to 7 g/cm$^3$, preferably 0.9 to 5 g/cm$^3$.

In a particular embodiment of the present invention, the nanofibres in the network are 2 to 100 km long.

In a particular embodiment of the present invention, the nanofibres in the network are as long as the nanofibre nonwoven.

In particular, the invention also relates to a second method for producing a nanofibre nonwoven according to the invention, comprising the following method steps:

a') providing at least one nanofibre material and at least one porogen material suitable for the formation of at least one porogen, b') electrospinning the at least one nanofibre material while introducing at least one porogen formed from the at least one porogen material having a diameter of 30 to 1000 μm, so that the ratio of porogen material to nanofibre material in the electrospun nanofibre nonwoven obtained after completion of this method step is 95 to 99 to 5 to 1 (in each case by mass, based on the total mass, i.e. porogens and fibres, of the nanofibre nonwoven), and c') obtaining a nanofibre nonwoven comprising at least one porogen, in particular a nanofibre nonwoven having a porosity of 90.0 to 99.9 vol. %, in particular 92.5 to 99.9 vol. %, in particular 95.0 to 99.9 vol. %, in particular 98.5 to 99.9 vol. % (in each case based on the total volume of the nanofibre nonwoven).

In a particularly preferred embodiment, the ratio of porogen material to nanofibre material in the electrospun nanofibre nonwoven obtained after completion of method step b') according to a first method is 96 to 99 to 4 to 1, in particular 97 to 99 to 3 to 1, in particular 98 to 99 to 2 to 1, in particular 95 to 98 to 5 to 2, in particular 95 to 97 to 5 to 3, in particular 95 to 96 to 5 to 4, in particular 96 to 98 to 4 to 2 (in each case by mass, based on the total mass, i.e. porogens and nanofibre material, of the nanofibre nonwoven). Preferably, nanofibre nonwovens thus produced according to a first and/or second method have meshes with a width of at most $200 \, \mu m^2$, in particular at most $150 \, \mu m^2$, in particular at most $100 \, \mu m^2$, in particular at most $50 \, \mu m^2$ (in each case measured in water without porogen).

Particularly preferably, nanofibre nonwovens produced in this way have meshes with a width of 10 to $200 \, \mu m^2$ (measured in water without porogen). In a particularly preferred embodiment, nanofibre nonwovens produced according to a method according to the invention have meshes with a width of 20 to $200 \, \mu m^2$, in particular 10 to $150 \, \mu m^2$, in particular 20 to $150 \, \mu m^2$, in particular 10 to $100 \, \mu m^2$, in particular 20 to $100 \, \mu m^2$, in particular 10 to $50 \, \mu m^2$, in particular 20 to $50 \, \mu m^2$.

The invention also relates to aforementioned first and/or second methods for producing a nanofibre nonwoven, further comprising the method steps:

d) incubating the nanofibre nonwoven obtained in method step c) or c') comprising at least one porogen in at least one solvent to at least partially remove the at least one porogen from the nanofibre nonwoven; and e) obtaining a nanofibre nonwoven.

In particular, the invention also relates to nanofibre nonwovens produced by a first and/or second method further comprising method steps d) and e).

In a particularly preferred embodiment, the solvent for dissolving out the at least one porogen is a liquid suitable for this purpose, in particular a liquid that does not attack, in particular does not degrade, does not structurally alter or does not destroy the nanofibres formed from the nanofibre material.

In a particularly preferred embodiment, the liquid used as solvent is water. In a particularly preferred embodiment, the liquid is an aqueous solution, in particular of one or more substances. In a particularly preferred embodiment, the liquid is a non-aqueous or aqueous solution of a substance or mixture of substances inert to the nanofibre material in a solvent, for example water.

In a particularly preferred embodiment, the solvent in the form of an aqueous solution has a pH of 1 to 13, in particular 1 to 11, in particular 2 to 11, in particular 3 to 11, in particular 5 to 9, preferably 6 to 8, in particular 7.

In a particularly preferred embodiment, when calcium carbonate has been used as the porogen material for producing the nanofibre nonwoven, the pH of the solvent carried out as an aqueous solution is 4 to 5, in particular 4.5.

In a particularly preferred embodiment, when chitosan has been used as the porogen material for producing the nanofibre nonwoven, the pH of the solvent carried out as an aqueous solution is 2 to 4, in particular 3.

In a particularly preferred embodiment, when zinc oxide has been used as porogen material for producing the nanofibre nonwoven, the pH of the solvent carried out as an aqueous solution is 1 to 3, in particular 2.

In a particularly preferred embodiment, when silica gel/amorphous silica has been used as porogen material for producing the nanofibre nonwoven, the pH of the solvent carried out as an aqueous solution is 11 to 13, in particular 12.

In a preferred embodiment, after dissolving out the porogens, in particular all porogens, the solvent is replaced by a liquid, in particular by an aqueous solution, in particular water.

Preferably, after dissolving out the porogens, in particular all the porogens, a liquid is added to the nanofibre nonwoven according to the invention, in particular water, so that a nanofibre nonwoven according to the invention having at least one liquid is obtained.

In a preferred embodiment of the present invention, after dissolving out all or a part of the porogens, at least one liquid, in particular water, is added to the nanofibre nonwoven in an amount such that the at least one liquid and any possibly porogens still present in the nanofibre nonwoven have a volume of 90.0 to 99.9 vol. %, in particular 92.5 to 99.9 vol. %, in particular 95.0 to 99.9 vol. %, in particular 98.5 to 99.9 vol. % of liquid and optionally porogens (in each case based to the total volume of the nanofibre nonwoven).

The invention also relates to a first and/or second method mentioned above for producing a nanofibre nonwoven, wherein the porogen material provided in method step a) or a') is particulate or fibrous, has a diameter of 30 to $1000 \, \mu m$, in particular 40 to $1000 \, \mu m$, in particular 50 to $1000 \, \mu m$, in particular 70 to $1000 \, \mu m$, in particular 100 to $1000 \, \mu m$, in particular 30 to $500 \, \mu m$, in particular 40 to $500 \, \mu m$, in particular 50 to $500 \, \mu m$, in particular 70 to $500 \, \mu m$, in particular 100 to $500 \, \mu m$, in particular 30 to $250 \, \mu m$, in particular 40 to $250 \, \mu m$, in particular 50 to $250 \, \mu m$, in particular 70 to $250 \, \mu m$, in particular 100 to $250 \, \mu m$, in particular 30 to $150 \, \mu m$, in particular 40 to $150 \, \mu m$, in particular 50 to $150 \, \mu m$, in particular 70 to $150 \, \mu m$, in particular 100 to $150 \, \mu m$, and is provided in method step a) or a') as a formed porogen.

In a particularly preferred embodiment, the porogen material provided in method step a) or a') has a diameter of 30 to $1000 \, \mu m$, in particular 40 to $1000 \, \mu m$, in particular 50 to $1000 \, \mu m$, in particular 70 to $1000 \, \mu m$, in particular 100 to $1000 \, \mu m$, in particular 30 to $500 \, \mu m$, in particular 40 to $500 \, \mu m$, in particular 50 to $500 \, \mu m$, in particular 70 to $500 \, \mu m$, in particular 100 to $500 \, \mu m$, in particular 30 to $250 \, \mu m$, in particular 40 to $250 \, \mu m$, in particular 50 to $250 \, \mu m$, in particular 70 to $250 \, \mu m$, in particular 100 to $250 \, \mu m$, in particular 30 to $150 \, \mu m$, in particular 40 to $150 \, \mu m$, in particular 50 to $150 \, \mu m$, in particular 70 to $150 \, \mu m$, in particular 100 to $150 \, \mu m$, wherein at least 70%, in particular at least 80%, in particular at least 90%, in particular at least 95%, in particular at least 99%, in particular 100%, of the porogen material provided in method step a) or a') has a diameter of at least $30 \, \mu m$, in particular at least $40 \, \mu m$, in particular at least $50 \, \mu m$, in particular at least $70 \, \mu m$, in particular at least $100 \, \mu m$.

In a particularly preferred embodiment, at least 70%, in particular at least 80%, in particular at least 90%, in particular at least 95%, in particular at least 99%, in particular 100%, of the porogen material provided in method step a) or a') has a diameter of 30 to $1000 \, \mu m$, in particular 40 to $1000 \, \mu m$, in particular 50 to $1000 \, \mu m$, in particular 70 to $1000 \, \mu m$, in particular 100 to $1000 \, \mu m$, in particular 30 to $500 \, \mu m$, in particular 40 to $500 \, \mu m$, in particular 50 to $500 \, \mu m$, in particular 70 to $500 \, \mu m$, in particular 100 to $500 \, \mu m$, in particular 30 to $250 \, \mu m$, in particular 40 to $250 \, \mu m$, in particular 50 to $250 \, \mu m$, in particular 70 to $250 \, \mu m$, in particular 100 to $250 \, \mu m$, in particular 30 to $150 \, \mu m$, in particular 40 to $150 \, \mu m$, in particular 50 to $150 \, \mu m$, in particular 70 to $150 \, \mu m$, in particular 100 to $150 \, \mu m$.

Insofar as, in a particularly preferred embodiment of the invention, the porogen is provided in method step a) or a') as a ready-formed porogen, in method step b) or b') preferably an introducing of the porogens and the electrospinning of the nanofibre material is carried out alternately.

The invention also relates to a method as mentioned above for producing a nanofibre nonwoven, wherein the porogen material provided in method step a) or a') is a material suitable for forming at least one fibrous porogen, and in method step b) or b') at least one fibrous porogen is formed from the porogen material before or during its introduction into the electrospun nanofibre material, in particular continuously, in particular continuously and simultaneously.

In a particularly preferred embodiment, the porogen material is formed into one or more fibrous porogens by means of pressure spinning in method step b) or b'), in a particularly preferred embodiment during the introduction of the porogen material into the electrospun nanofibre material in method step b) or b').

In a preferred embodiment, a fibrous porogen is applied to the electrospun nanofibre material by unwinding from a spindle in method step b) or b').

In a preferred embodiment, electrospinning in method step b) or b') is performed using a grounded rotating roller or a grounded plate.

In a preferred embodiment, the porogen material is applied to the electrospun nanofibre material using 3D printing methods, in particular fused deposition modelling (FDM), bioprinting/bioplotting, selective laser scintering or melt electro writing (MEW), in method step b) or b').

In a preferred embodiment, the porogen material is applied to the electrospun nanofibre material by ink-jet method in method step b) or b').

In a preferred embodiment, the adhesive strength of the at least one porogen material is increased prior to introduction in method step b) or b'), preferably by partially treating the surface of the porogen material with a solvent in which the porogen material dissolves only slightly, in particular with a solubility of at most 0.5 g porogen material/100 g solvent, in particular at most 0.2 g porogen material/100 g solvent, in particular exactly 0.065 g porogen material/100 g solvent in each case at 25° C., wherein the porogen material is preferably present in particulate or fibrous form, in particular in particulate form.

In a particularly preferred embodiment of the present invention, in method step b) or b') the electrospinning is carried out at airspeeds of 1 to 100 m/s, in particular 5 to 50 m/s, in particular 8 to 30 m/s.

In a preferred embodiment of the present invention, electrospinning in method step b) or b') is carried out continuously, in particular continuously and simultaneously.

In a preferred embodiment of the present invention, the electrospinning in method step b) or b') is carried out alternately.

In a particular embodiment of the present invention, the nanofibre nonwoven obtained in method step c) or c') is subsequently mechanically processed, in particular cut. The present invention also relates to nanofibre nonwovens, producible or produced according to one of the methods according to the invention, in particular the first or second method. In a preferred embodiment, such nanofibre nonwovens are also referred to as nanofibre nonwovens according to the invention.

The invention also relates to the use of a nanofibre nonwoven according to the invention for the cultivation or differentiation of cells.

The invention also relates to an artificial tissue comprising at least one nanofibre nonwoven according to the invention and at least one cell of at least one cell type, optionally together with extracellular matrix. The invention also relates to an artificial tissue comprising at least one nanofibre nonwoven according to the invention and cells of at least one cell type, optionally together with extracellular matrix.

In a preferred embodiment of the invention, the at least one cell type is selected from the group consisting of fibroblasts, in particular cancer associated fibroblasts, keratinocytes, mesenchymal stem cells, iPS cells (induced pluripotent stem cells), tumour cells, endothelial cells and combinations thereof.

In a preferred embodiment, the artificial tissue has several, in particular at least two, in particular at least three, nanofibre nonwovens according to the invention.

The invention also relates to an artificial tissue comprising a nanofibre nonwoven according to the invention and cells of at least one cell type, wherein the artificial tissue comprises 1 to 50 wt. % nanofibre nonwoven and 50 to 99 wt. % cells, in particular 80 to 99 wt. % cells and, optionally, extracellular matrix, in particular 1 to 49 wt. % extracellular matrix (in each case based on the total weight of the artificial tissue).

The invention also relates to an artificial tissue comprising a nanofibre nonwoven according to the invention and cells of at least one cell type, wherein the artificial tissue comprises 1 to 50 wt. % nanofibre nonwoven and 50 to 99 wt. % cells (in each case based on the total weight of the artificial tissue).

The invention also relates to an artificial tissue comprising a nanofibre nonwoven according to the invention and cells of at least one cell type, wherein the artificial tissue comprises 1 to 49 wt. % nanofibre nonwoven and 50 to 99 wt. % cells and 1 to 49 wt. % extracellular matrix (each based on the total weight of the artificial tissue).

The invention also relates to an artificial tissue, wherein the at least one porogen present in the nanofibre nonwoven has been at least partially removed from the nanofibre nonwoven prior to colonizing with cells.

In a preferred embodiment, the artificial tissue is a skin model, in particular comprising a dermis, comprising at least one nanofibre nonwoven according to the invention. In a preferred embodiment, the artificial tissue is a skin model, preferably comprising a subcutis comprising at least one nanofibre nonwoven according to the invention.

In a preferred embodiment, the artificial tissue is a skin model, in particular comprising a dermis comprising at least one nanofibre nonwoven according to the invention and a subcutis comprising at least one nanofibre nonwoven according to the invention, preferably a different nanofibre nonwoven.

Preferably, the at least two nanofibre nonwovens used in the skin model according to the invention have a specific formation, in particular they each have at least one cell of a specific cell type, in particular of a different cell type.

The invention also relates to a method for producing an artificial tissue comprising the following method steps:

x1) providing at least one cell of at least one cell type, a culture medium and at least one nanofibre nonwoven according to the invention, x2) optionally removing at least a part of an optionally present at least one porogen, x3) cultivating the at least one nanofibre nonwoven with the at least one cell in the culture medium, and x4) obtaining an artificial tissue comprising at least one cell arranged on or in the at least one nanofibre nonwoven.

In a preferred embodiment of the present invention, during the cultivation provided in method step x3), colonisation of the nanofibre nonwoven according to the invention occurs through the meshes of the nanofibre nonwoven into the pores of the nanofibre nonwoven, preferably and optionally followed by contraction of the pores resulting in a three-dimensional artificial tissue according to the invention comprising nanofibres, cells and proteins formed by these.

In a preferred embodiment, the cells are homogeneously distributed within the nanofibre nonwoven according to the invention and, in a further preferred embodiment, lead to a homogeneous distribution of the extracellular matrix, in particular of the proteins.

The invention also relates to such a method, wherein during or after the cultivation according to method step x3) the nanofibre nonwoven is cultivated in a method step x31) with at least one cell of at least one further cell type, in particular a cell type different from the cell type provided in method step x1).

The invention also relates to such a method, wherein during or after the cultivation according to method step x3) or x31) further nanofibre nonwovens, preferably colonized with cells of an identical or different cell type, are stacked on the nanofibre nonwoven obtained in x3) or x31).

In a preferred embodiment of the invention, 20,000 to 150,000 cells/cm$^2$, in particular 40,000 to 100,000 cells/cm$^2$, of the at least one cell type are provided in method step x1) in the method for producing an artificial tissue.

In a preferred embodiment of the invention, the at least one nanofibre nonwoven according to the invention is clamped in a cell crown or Transwell® insert in a method step x21).

In the context of the present invention, a "cell crown" is understood to mean two rings of different sizes, preferably stainless steel rings, which can be inserted into each other in such a way that a nanofibre nonwoven is partially clamped between them and thus a part of the nanofibre nonwoven is stretched over the free space of the smaller ring.

The present invention also relates to therapeutic applications of nanofibre nonwovens of the invention and artificial tissues having the same.

The present invention also relates to methods for the therapy of, in particular, diseased, humans or animals, and to products for use in such methods.

In particular, the nanofibre nonwoven according to the invention can be used as a wound insert, in particular for the therapy of preferably chronic wounds or burn wounds, in particular with introduction, in particular insertion, of the high-porosity nanofibre nonwoven according to the invention into wounds, colonizing with tissue cells from the wound edges, sealing of the wound over the nanofibre nonwoven according to the invention by cells, in particular keratinocytes.

The nanofibre nonwoven according to the invention can also be used as a porous tissue which allows in vivo ingrowth of cells during regeneration after, for example, surgical interventions or resections in (cancer) therapy.

In particular, the present invention also relates to methods for the therapy of, in particular, diseased humans or animals using the artificial tissue according to the invention and the artificial tissue according to the invention for use in such methods. In particular, the artificial tissue according to the invention can be used as an ATMP (Advanced Therapy Medicinal Product), in a preferred embodiment colonized with tissue-specific cells, wherein the use in or as stromal or stromal tissue/organ(s) is preferred, in particular in or as skin, cartilage, arteries and/or veins, heart, kidney, liver, urogenital tract, respiratory tract, bone, intestine or cornea.

The present invention also relates to non-therapeutic applications of nanofibre nonwovens according to the invention and artificial tissues comprising them, for example cosmetic applications.

In the context of the present invention, the volume ratio of porogen material to nanofibre material in the electrospun nanofibre nonwoven obtained after completion of electrospinning is determined by determining the volumes of porogen material and nanofibre material present in the obtained electrospun nanofibre nonwoven. The volumes of the porogen material and nanofibre material contained in the obtained electrospun nanofibre nonwoven can be determined by determining the mass of the porogen material and nanofibre material present in the obtained electrospun nanofibre nonwoven, taking into account the known density of the porogen material and nanofibre material present in the obtained electrospun nanofibre nonwoven.

In the context of the present invention, the term "and/or" is understood to mean that all members of a group which are connected by the term "and/or" are represented both cumulatively with each other in any combination, and alternatively with each other. Exemplarily, for the expression "A, B and/or C", the following disclosure is to be understood thereunder: i) (A or B or C), or ii) (A and B), or iii) (A and C), or iv) (B and C), or v) (A and B and C), or vi) (A and B or C), or vii) (A or B and C), or viii) (A and C or B).

In the context of the present invention, individual components or constituents of an assembly, in particular of the nanofibre nonwoven according to the invention or of one of its components, determined quantitatively in relative form, in particular in percentages, preferably add up to 100 wt. % of the respective assembly or nanofibre nonwoven referred to or, if referred to, of a component thereof, unless otherwise stated.

In the context of the present invention, unless otherwise indicated, unstated decimal places of a decimal number are understood as 0.

LIST OF REFERENCE SIGNS 1 z-direction, also referred to as height or thickness.
2 x-direction, also referred to as width
3 y-direction, also referred to as depth
4 nanofibre layers
5 pores
6 porogens, in particular soluble porogens
7 nanofibres
8 mesh, shaded area denotes mesh size
9 pore width
10 pore depth
11 pore height
12 nanofibre nonwoven thickness/nanofibre nonwoven height
13 nanofibre nonwoven width (a main (surface) expansion direction of the nanofibre nonwoven)
14 nanofibre nonwoven depth (a main (surface) expansion direction of the nanofibre nonwoven)
100 nanofibre nonwoven according to the invention Further advantageous embodiments of the invention are apparent from the subclaims.

The following examples and the accompanying figures explain the present invention without, however, limiting it.

The figures show:

FIG. 1 Examples of structures of high-porosity nanofibre nonwovens according to the invention. (A) High-porosity nanofibre nonwoven with randomly oriented nanofibres (7), imaged in water by confocal reflection microscopy. (B) Porous structure of the randomly oriented nanofibre nonwoven, prepared by a paraffin section and imaged through an optical microscope with subsequent image processing. (C) High-porosity nanofibre nonwoven with oriented nanofibres (7), imaged as (A). (D) Porous structure of the oriented nanofibre nonwoven, prepared and photographed as in (B).

Figure 2:
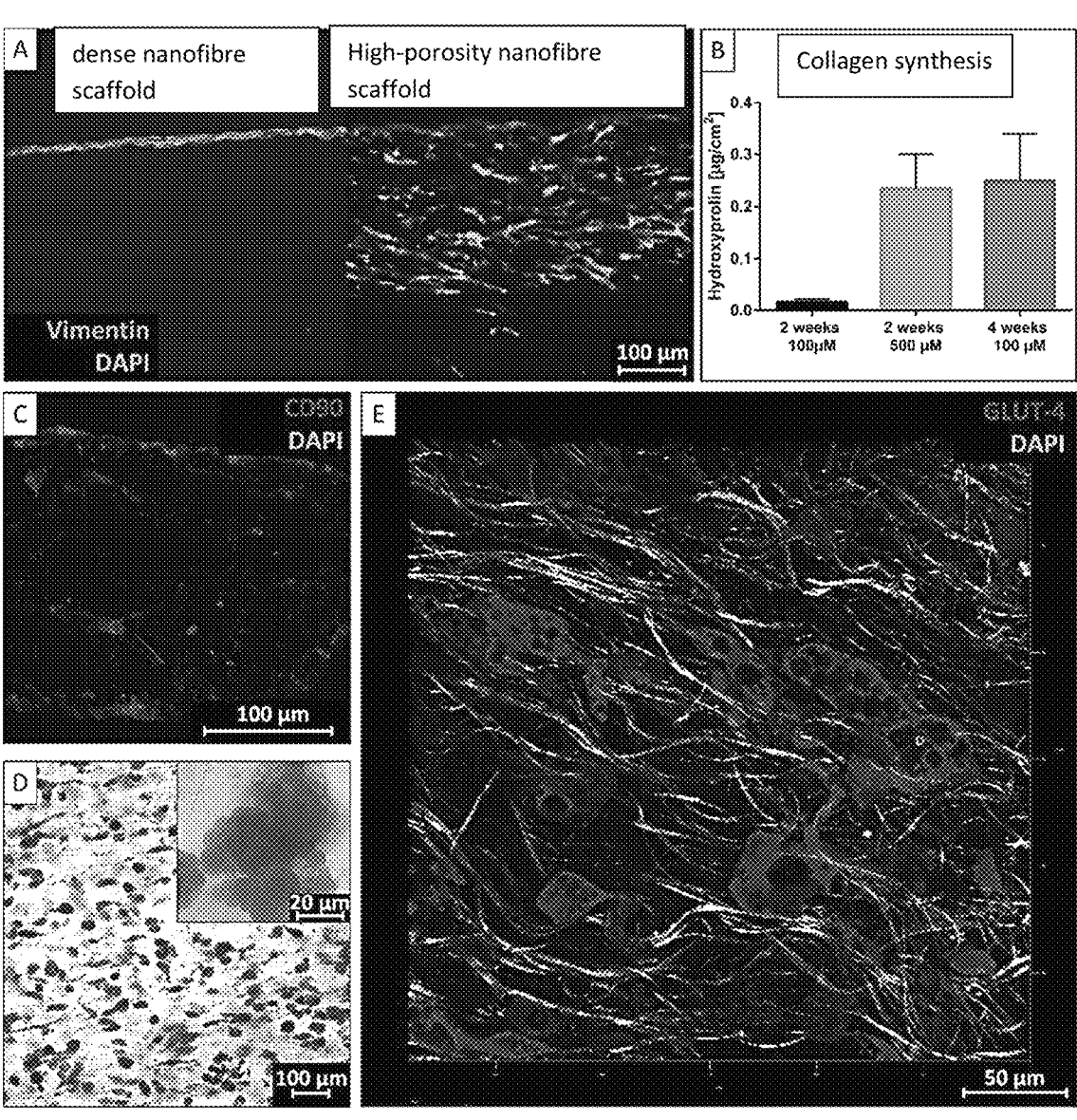

FIG. 2 Properties of the high-porosity nanofibre nonwoven according to the invention in relation to biological processes. (A) Compared to a dense nanofibre nonwoven not according to the invention, fibroblasts can colonise the entire high-porosity nanofibre nonwoven independently. (B) During colonization, these cells are able to synthesise tissue such as collagen within the nanofibre nonwoven. (C) These migration properties in the high-porosity nanofibre nonwoven are present for all types of tissue cells, such as MSCs. (D, E) MSCs in particular can be differentiated within the nanofibre nonwoven, for example in the adipogenic direction.

Figure 3:
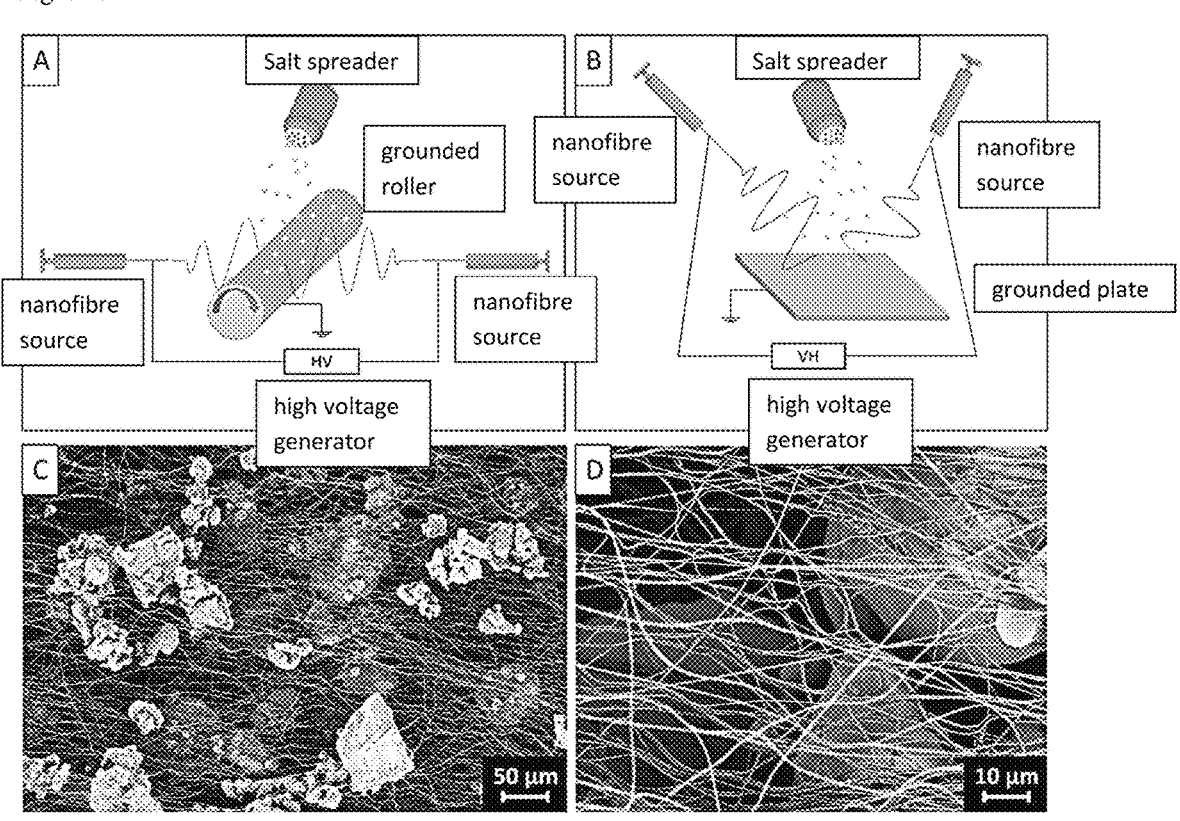

FIG. 3 Production of high-porosity nanofibre nonwovens with particles according to the invention (A) Schematic drawing of the spinning set-up with rotating cylindrical collector, particle addition and horizontally opposed nanofibre sources. (B) Schematic setup with collector plate instead of cylinder. (C) SEM image of NaCl particles within the nanofibre nonwoven, (D) and close-up image of the nanofibres (7).

Figure 4:
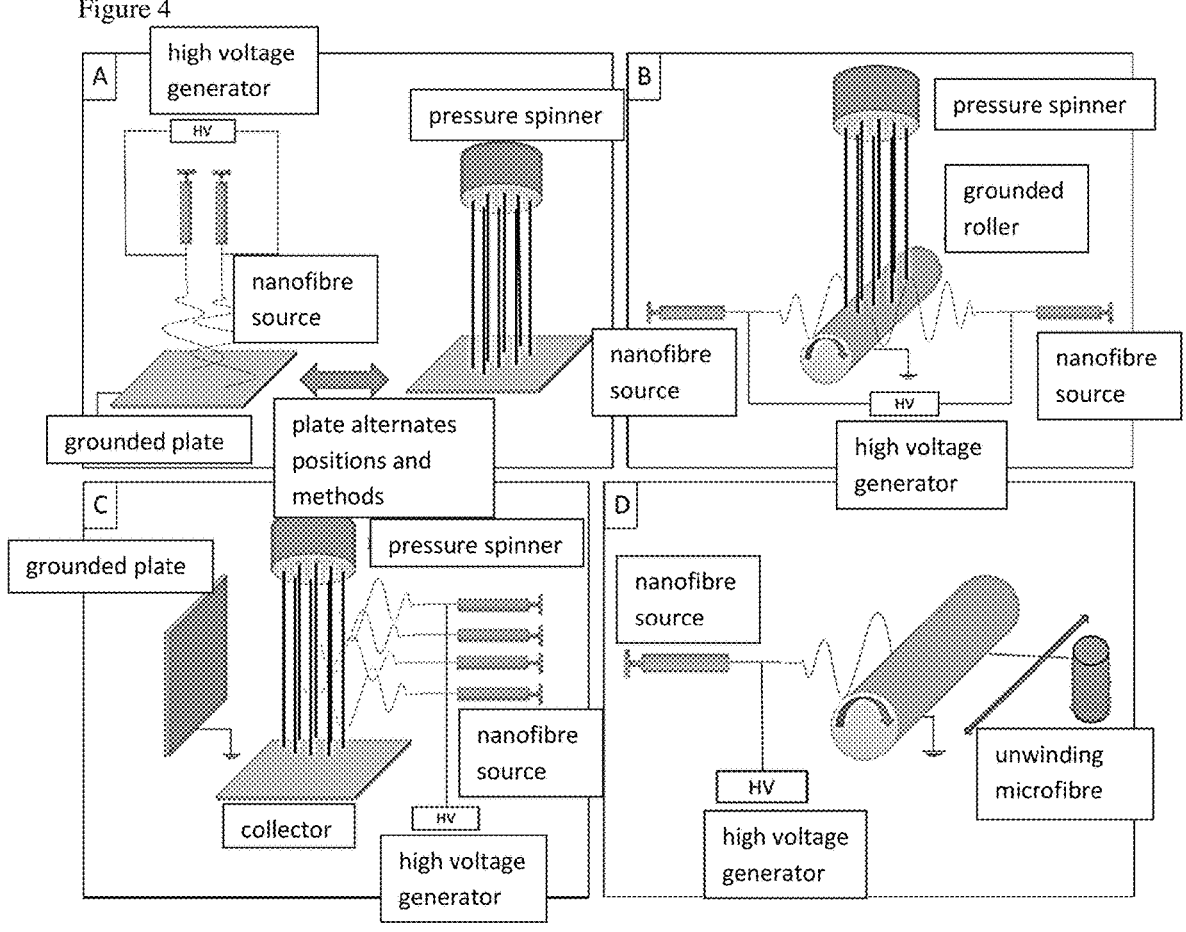

FIG. 4 Production of high-porosity nanofibre nonwovens according to the invention in combination with fibres in the micrometre range. (A) Schematic drawing of the combination electro-spinning/pressure spinning alternately on a plate. (B) Schematic presentation of the combination electro-spinning/pressure spinning simultaneously on a rotating cylinder. (C) Schematic set-up of the combination electro-spinning/pressure spinning, wherein the nanofibres (7) are spun directly into the flow of the microfibres. (D) Schematic drawing of the combination electro-spinning with an already produced fibre, which is continuously wound between the nanofibres (7) on the rotating cylinder during the e-spinning process.

Figure 5:
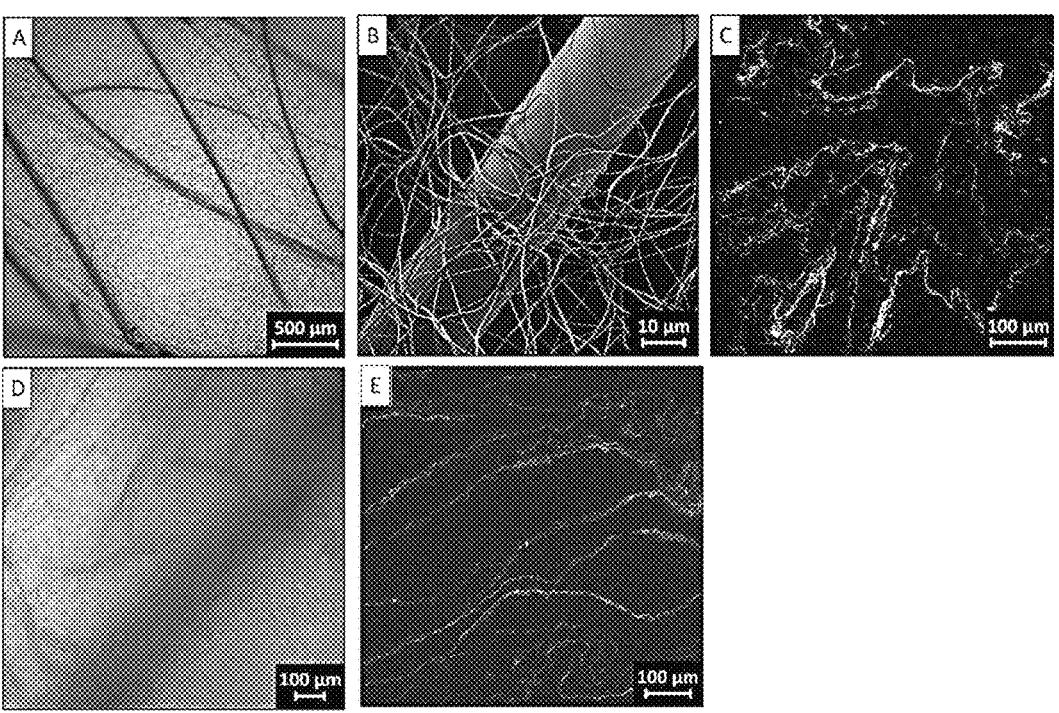

FIG. 5 Microscopy of the fibre structure by combining electrospinning with microfibres. (A) Light microscope image of pressure-spun fibres and the combined nanofibres (7) (method: FIG. 4A). (B) SEM image shows the dimensional difference of the two fibres. (C) After dissolving out the microfibres, the cross-section describes high porosity. (D) Light microscope image of nanofibres (7) combined with a simultaneously wound thread in the micrometre range (method: FIG. 4D). (E) After detaching the microfibres, the cross-section describes a high porosity.

Figure 6:
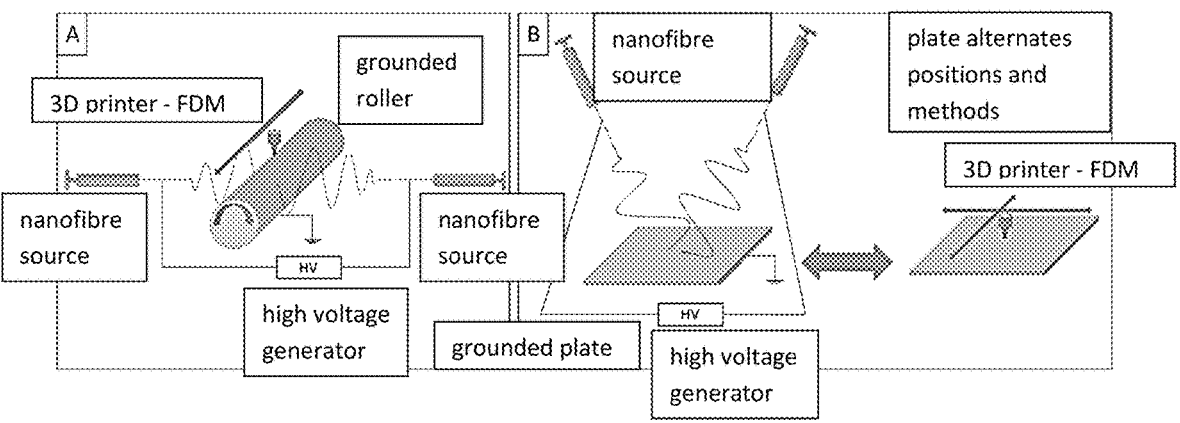

FIG. 6 Production of high-porosity nanofibre nonwovens according to the invention in combination with FDM or MEW. (A) Schematic presentation of the combination E-spinning/3D-printing simultaneously on a rotating cylinder. (B) Schematic drawing of the combination E-spinning/pressure spinning alternately on a plate.

Figure 7:
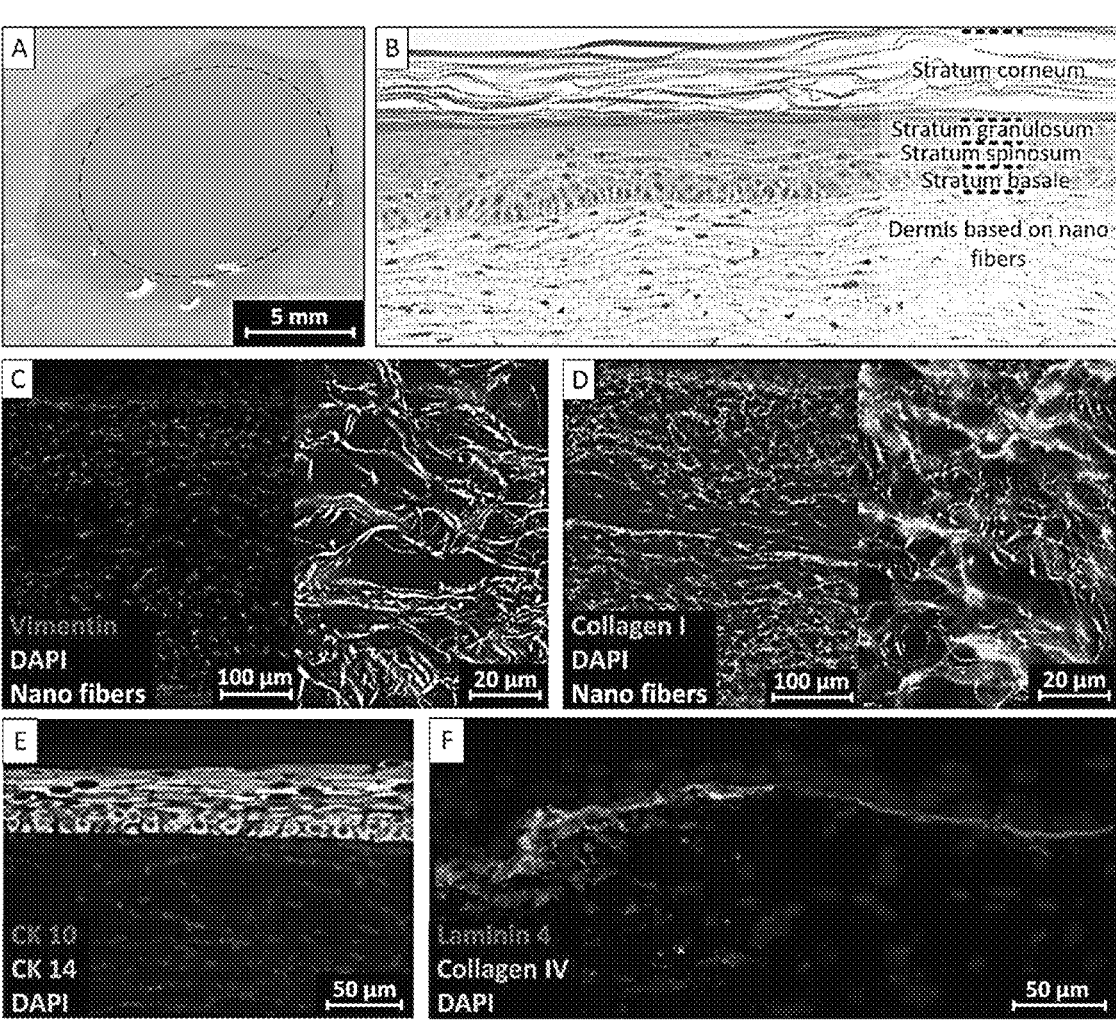

FIG. 7 Application example of high-porosity nanofibre nonwovens according to the invention in 3D tissue culture—skin from dermis and epidermis. (A) Photo of an in vitro generated skin model. (B) HE staining of the cross-section describes the individual physiological layers of the epidermis, as well as partially the nanofibre-based dermis. (B) IF staining against vimentin shows the homogeneous distribution of fibroblasts in the dermal high-porosity non-woven. The right part shows the fibres and fibroblasts simultaneously in a higher magnification. (D) IF staining against collagen I describes the distribution of the synthesised DCM. The right part shows the fibres and the biological matrix simultaneously in a higher magnification. (E) IF staining against cytokeratin 10 and 14, as well as against (D) laminin and collagen 4 show the reconstructed physiological areas of the epidermis.

Figure 8:
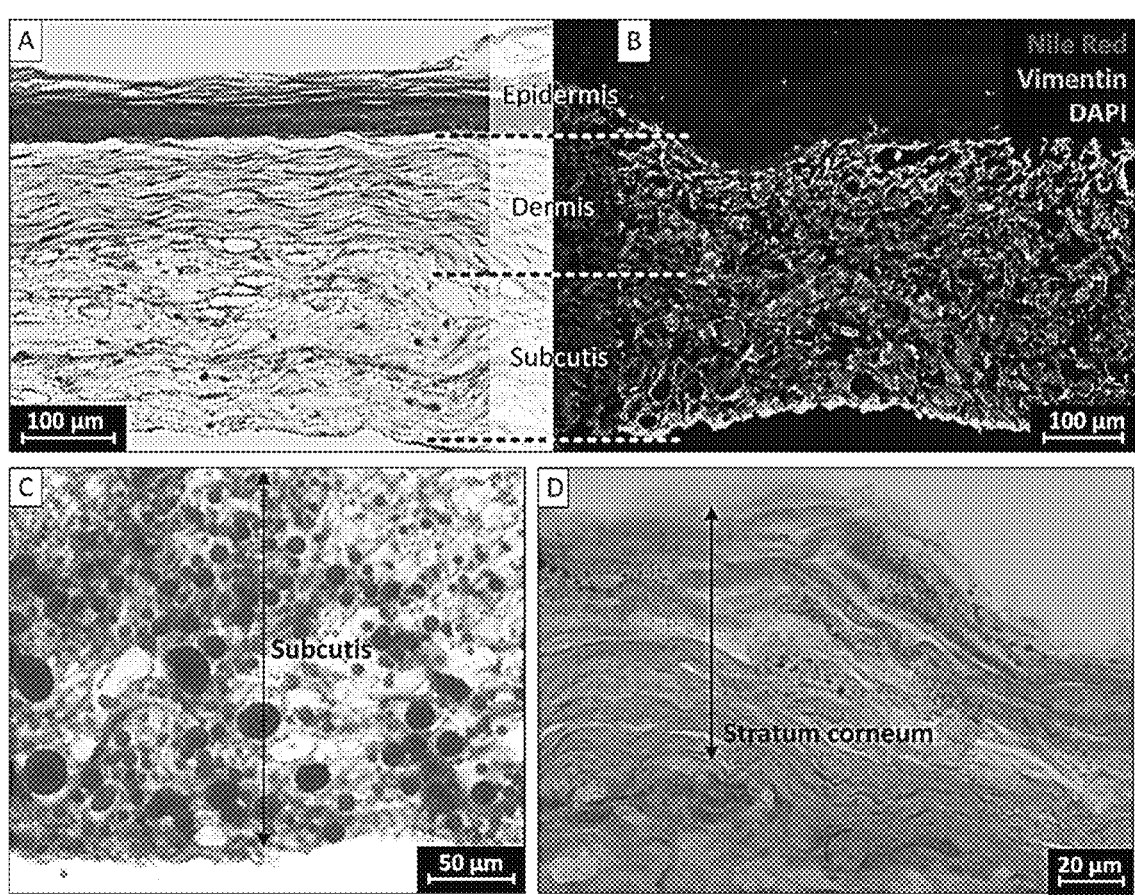

FIG. 8 Application example of high-porosity nanofibre nonwovens according to the invention in 3D tissue culture— skin from subcutis, dermis and epidermis. (A) HE staining of the cross-section describes the individual physiological layers of the three-layer skin model. The empty vesicles in the subcutis represent the adipogenic cells. (B) IF staining against vimentin with Nile Red shows the homogeneous distribution of fibroblasts in the high-porosity non-woven, as well as the fat droplets in the deeper part of the model. (E) Presentation of the subcutis by staining the fat droplets with Oil Red. (D) In addition to the subcutis, nanoscale fat droplets within the epidermis can also be stained and imaged.

Figure 9:
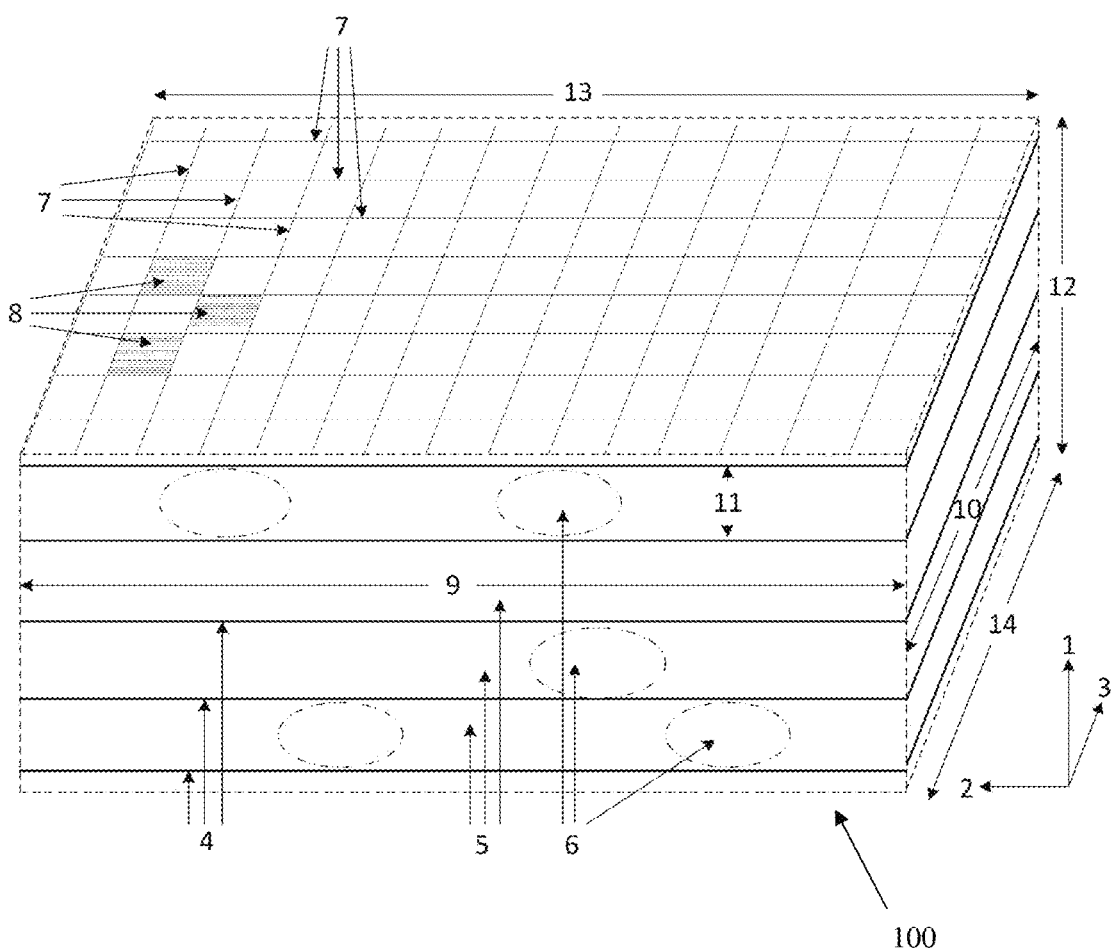

FIG. 9 Schematic drawing of a nanofibre nonwoven according to the invention to explain the relationship between the individual structural components of a nanofibre nonwoven according to the invention.

Shown is a nanofibre nonwoven 100 according to the invention, its extension in the z-direction 1 and the surface extension directions 2 and 3 in the x- and y-directions. The nanofibre layers 4, the pores 5, the porogens 6, the nanofibres 7 and the meshes 8 formed by the nanofibres are shown. The pore width 9, pore depth 10 and pore height 11 as well as the nanofibre nonwoven thickness or height 12, the nanofibre nonwoven width, namely a main expansion direction of the nanofibre nonwoven 13 as well as the nanofibre nonwoven depth, namely a further main expansion direction of the nanofibre nonwoven 14 are also shown.

Figure 10:
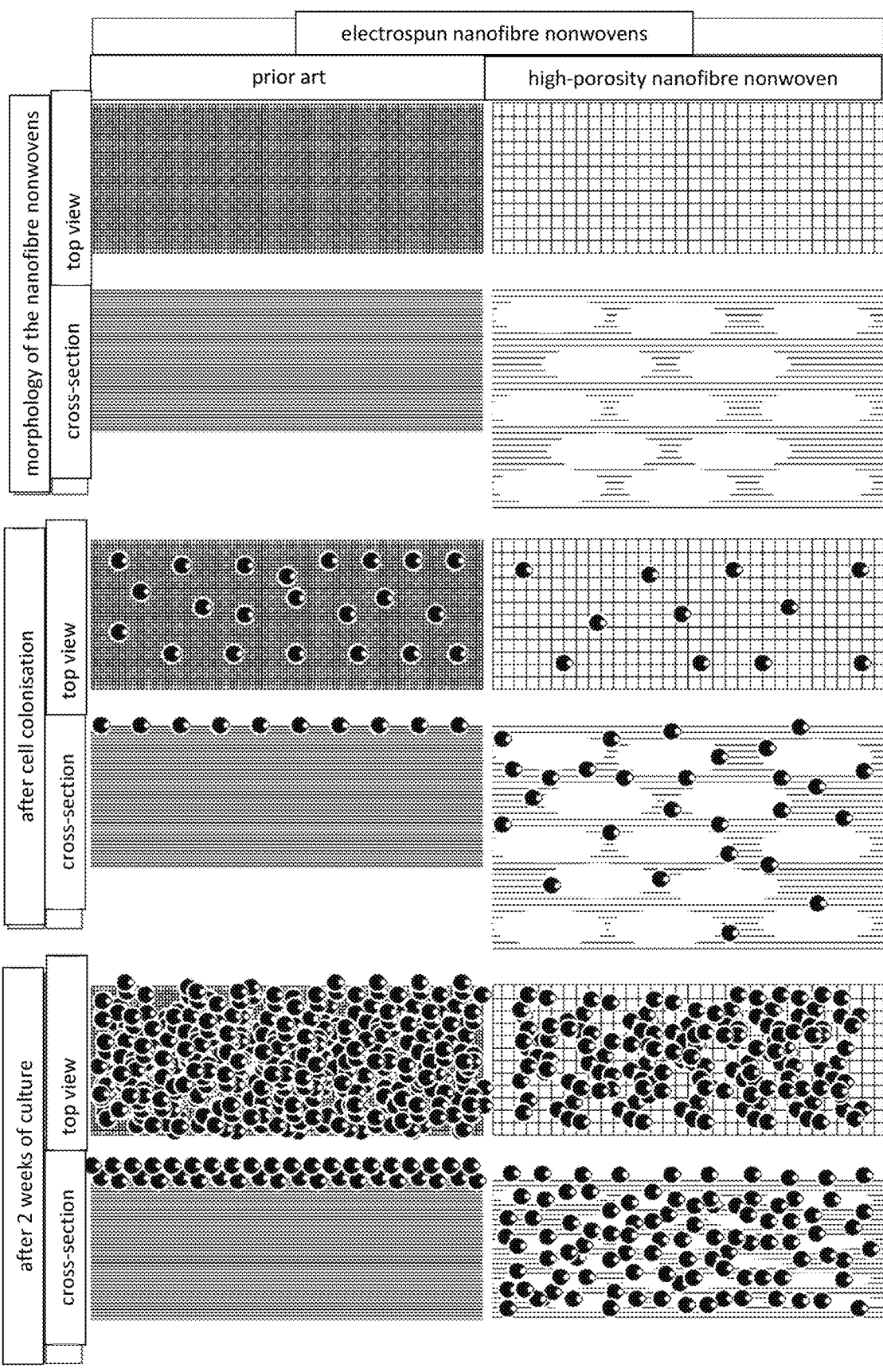

FIG. 10 Schematic drawing of the colonization of a nanofibre nonwoven not according to the invention (prior art) (left side) and a high-porosity nanofibre nonwoven according to the invention (right side) with cells (black dots with a smaller white dot).

Part 1: Morphology of the Nanofibre Nonwoven

Looking at the nanofibre nonwoven from above, the high-porosity nanofibre nonwoven according to the invention has much larger free spaces between the nanofibres (7) (referred to as meshes (8)). While these are limited to about 5 $\mu m^2$ in dense nanofibre nonwovens not according to the invention, the meshes of the high-porosity nanofibre nonwovens according to the invention can reach penetration areas of more than 100 $\mu m^2$. In cross-section, nanofibres (7) are deposited directly on top of each other in the dense nanofibre nonwoven not according to the invention. In contrast, the high-porosity nanofibre nonwoven according to the invention has pores (5) within the nanofibre nonwoven, which are created by porogens (6). These pores (5) can be closed laterally, but can also penetrate the entire nanofibre nonwoven in the surface expansion direction (13, 14). Furthermore, the nanofibres (7) in the high-porosity nanofibre nonwoven according to the invention are not always in direct contact with each other, which is why the distance between the nanofibres (7) is sometimes increased.

Part 2: After Cell Colonisation

If cells are added to the dense nanofibre nonwoven not according to the invention, they remain on the surface of the nanofibre nonwoven not according to the invention and proliferate there. In the case of the high-porosity nanofibre nonwoven according to the invention, the cells can completely penetrate the nanofibre nonwoven from top to bottom. As a result, considerably fewer cells remain on the surface of the high-porosity nanofibre nonwoven, but can proliferate strongly in the nanofibre nonwoven. The cells are able to move vertically (thickness/height of the nanofibre nonwoven, 12) through the nanofibre nonwoven over the enlarged meshes (8). In the width of the nanofibre nonwoven (13), the cells can move either along the surfaces of the pores (5) or through the enlarged spaces between the nanofibres (7).

Part 3: After 2 Weeks of Culture

After 2 weeks of culture, the cells on the dense nanofibre nonwoven not according to the invention have colonised the entire surface and (depending on the cell type) can proliferate further on top of each other, but do not penetrate the nanofibre nonwoven. In the high-porosity nanofibre nonwoven according to the invention, the cells mainly proliferate within the nonwoven. Thereby, the cells interact with the nanofibre nonwoven and tighten the highly flexible nanofibre nonwoven together. As a result, the cells within the pores (5) do not multiply directly on top of each other as on the surface of the dense nanofibre nonwoven not according to the invention. The contraction of the high-porosity nanofibre nonwoven according to the invention by the cells causes the pore height (11) in the nanofibre nonwoven to continuously decrease until they are no longer visible. As a result, the cells transform the nanofibre nonwoven in such a way that an almost homogeneous distribution of cells and nanofibres (7) is produced in all three spatial directions. After reaching a maximum cell density, the proliferation within the nanofibre nonwoven is reduced and takes place mainly on or under the nanofibre nonwoven.

Figure 11:
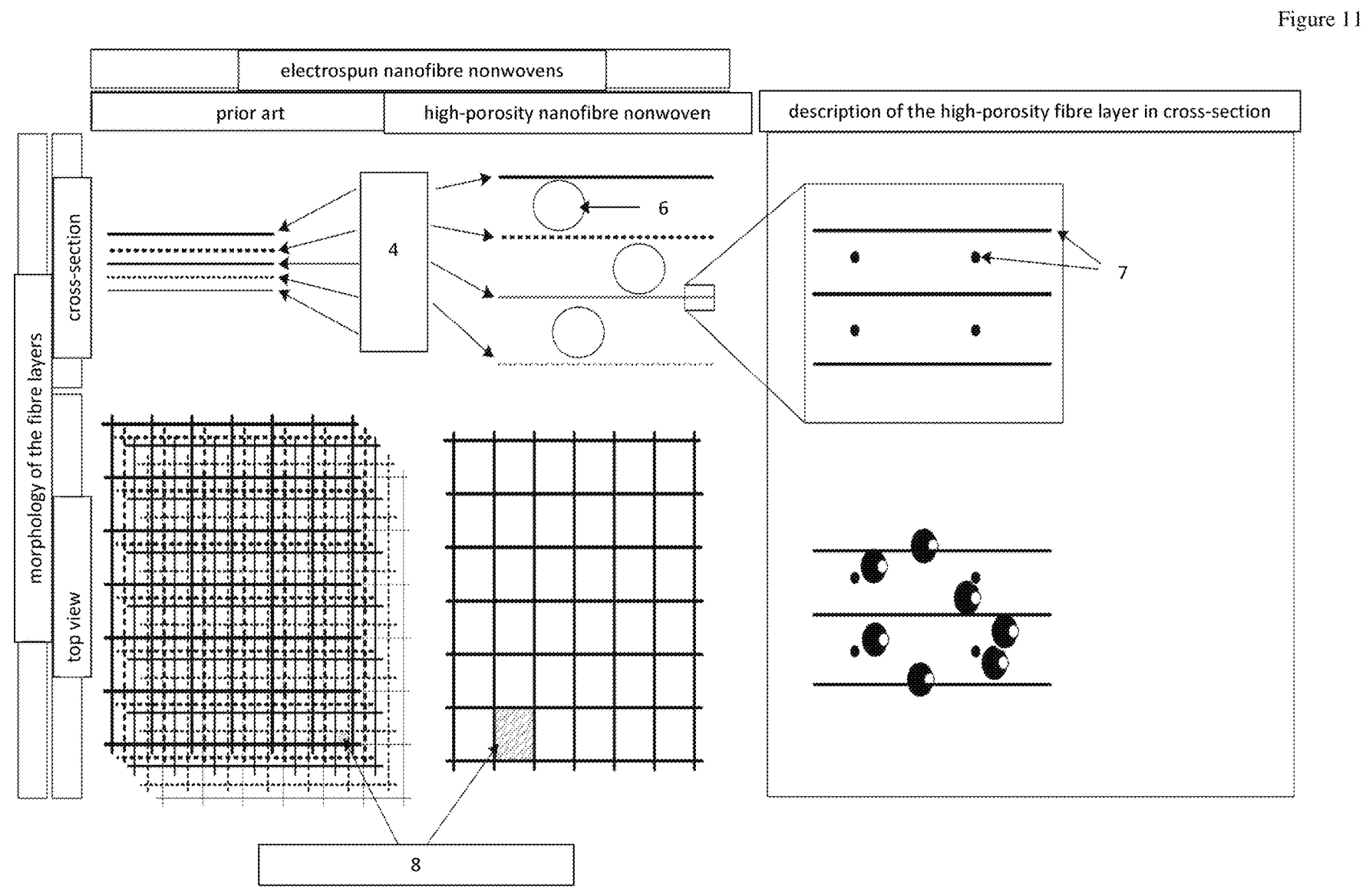

FIG. 11 Schematic drawing explaining the positioning of the meshes in a nanofibre nonwoven and the structure of the nanofibre nonwoven Part 1: Left Picture "Electron Spun Nanofibre Nonwoven".

In this context, nanofibre layers (4) are in particular thin fibre webs which are preferably separated from each other by porogens (6) during the production process. After the porogens (6) have been dissolved out, the nanofibre layers (4) remain separated from each other and form pores (5) filled with liquid. In the dense nanofibre nonwoven not according to the invention, no porogens (6) are incorporated, which is why there is no separation of the nanofibre layers (4) and they lie directly on top of each other. Due to the high number of nanofibres (7) and nanofibre layers (4) in direct contact with each other, the mesh size is reduced (viewed from above on the surface of the dense nanofibre nonwoven not according to the invention). The separation of the nanofibre layers (4) in the high-porosity nanofibre nonwoven according to the invention limits the number of nanofibres (7) on top of each other and thus guarantees the large mesh size (shaded area, 8) of the high-porosity nanofibre nonwoven according to the invention. In order to obtain this large mesh size (and thus to maintain accessibility by cells), it is preferable to keep the individual nanofibre layers constantly separated from each other by liquid, since attractive interactions between the nanofibres (7) can cause the pores (5) to disappear and thus greatly reduce the mesh size. Therefore, the high-porosity nanofibre nonwoven should preferably be kept permanently in liquid. In the case of a short-term transfer outside the liquid, it is preferable to ensure that the liquid does not flow completely out of the pores (5), so that the nanofibre layers (4) continue to be separated.

Part 2: Right Picture "Description of the High-porosity Nanofibre Layer in Cross-section".

Upper presentation: the individual nanofibre layers (4) of the high-porosity nanofibre nonwoven according to the invention consist of a limited number of free-moving nanofibres (7) on top of each other, which has the particular effect of obtaining a highly flexible nanofibre layer (4) with a dynamic structure. The number of superimposed nanofibres (all orientations, 7) is preferably between 1 and 25 individual fibres. A high number of nanofibres (7) may possibly have the effect of reducing the mesh size (shaded area, 8). In addition to the mesh size, the preferably low number of nanofibres in the nanofibre layer (4) has the effect that the points of contact between the nanofibres are minimised and the individual nanofibres (7) are also largely separated from one another across the thickness of the nanofibre layer (4). This allows the individual nanofibres (7) in the nanofibre layer (4) to move freely in all spatial directions.

Lower presentation: If cells (black dots with white smaller dots) are now added to the nanofibre layer (4), they can easily move between the nanofibres (7) and also move the individual nanofibres (7). This nanofibre layer (4) serves as a localised 3D cell scaffold. The nanofibre layer (4) remains highly flexible so that cell clusters can tighten the nanofibre layers (4) towards each other. If there are too many nanofibres (7) in the nanofibre layer, the mobility of the individual nanofibres (7) is considerably reduced and the 3D character of the nanofibre layer (4) is lost for the cells.

Figure 12:
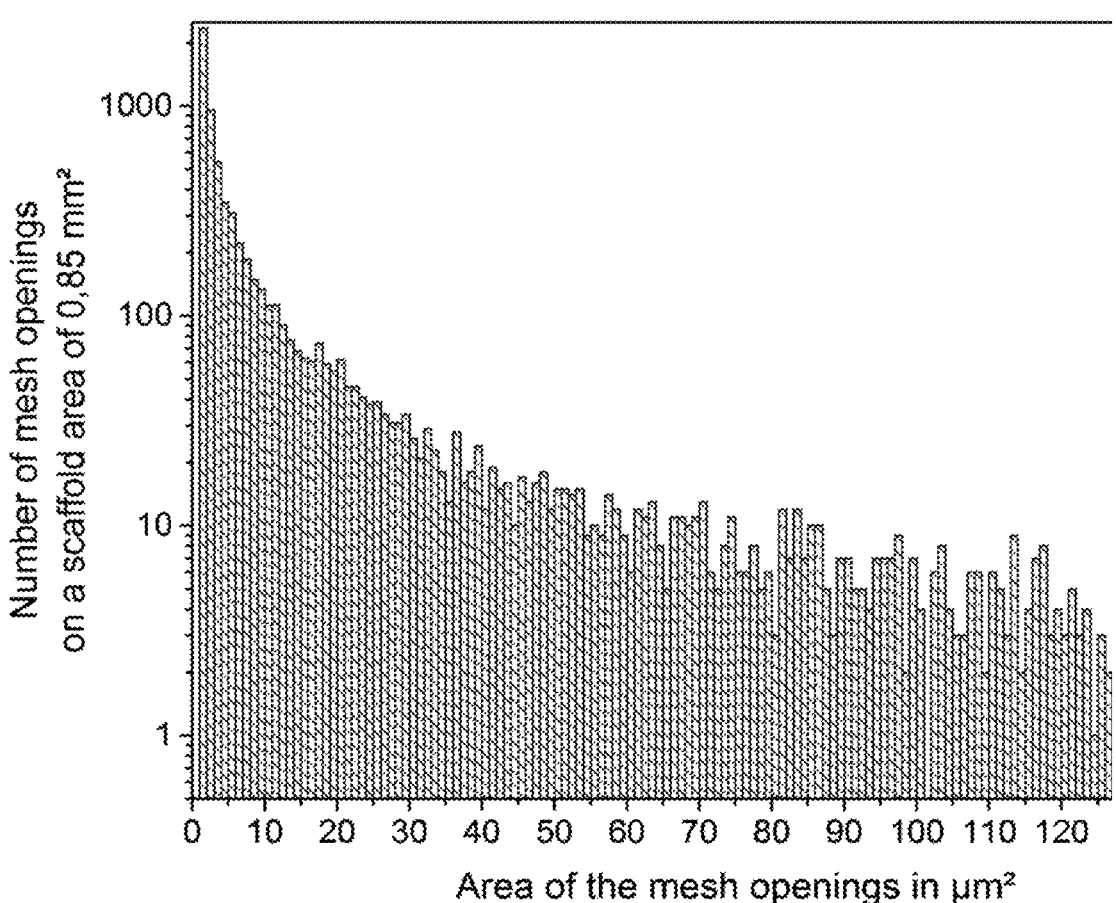

FIG. 12 Presentation of the number of meshes of certain mesh sizes in a nanofibre nonwoven according to the invention made of PA6 (polyamide) as nanofibre material, produced with NaCl particles as porogen and with a rotating roller during electrospinning according to example 1 (production example 1 "set-up of rotating roller"). The x-axis shows the area of the mesh size in $\mu m^2$ and the y-axis shows the number of meshes. The examined area of the piece of the nanofibre nonwoven was 0.85 $mm^2$.

EXAMPLES

Example 1

Production Examples/Combination of Electrospinning with Additive Manufacturing The production of high-porosity nanofibre nonwovens requires the insertion of structures in the range of 50-500 $\mu m$ between the nanofibres (7). This size range can be covered with different variants of additive manufacturing and can be run in automated or manual mode. In addition to these two possibilities, the combined method steps of method step b), namely electrospinning and insertion of the porogen (6), can be designed using an alternating or continuous process. Preferably in all methods, these micro-structures can be held on/between the nanofibres during the spinning process, in particular by the centrifugal forces when the roller is rotating.

Production Example 1: Particles

This producing variant uses particles as porogen (6) between the nanofibres (7). The particles can be dosed onto the nanofibre nonwoven manually by means of a spreader or via an automatically controlled spreading device. Two variants of the process are described below.

Material examples for these particulate porogens are: NaCl, NaCO$_3$, PEG/PEO, sugar.

Set-Up Rotating Roller:

In this setup, an alternating process can be run. This means that the spinning process is stopped after a certain time, the particles (6) are applied and then spinning continues (FIG. 3A). Due to the rotation of the roller, the adhesive force of the particles (6) on the nanofibres (7) must also be increased. In the case of water-soluble particles (for example NaCl, 6), the nanofibre surface is first moistened with ethanol and then sprinkled with particles (6). The low solubility of the porogen material dissolves the particles (6) superficially, thereby adhering them to the nanofibres (7). In this process, spinning can be done from two sides with at least one spinning source each.

For example, with this embodiment, a nanofibre nonwoven according to the invention could be produced, which comprises PA6 (polyamide) as nanofibre material and NaCl particles as porogen. The porosity of such a nanofibre nonwoven was 98.2% (measured by confocal reflection microscope).

The NaCl particles had a diameter of 30 to 80 μm.

The diameter of the nanofibres was 371±192 nm.

Set-Up Plate/Planar Surface

This set-up does not require any additional increase in porogen adhesion and can therefore be run using either a continuous or an alternating process. A spreader is placed centrally above the target, which evenly sprinkles the surface with the particles (6) (FIG. 3B). Somewhat to the side are the spin sources, which also distribute the nanofibres (7) as evenly as possible on the target. Depending on the size of the plate, a variety of scattering and spinning sources can be used. In the continuous process, it should be noted that the particulate porogen (6) does not interact with the electric field of the spinning sources and thus negatively influences the evenly scattering.

FIGS. 3 C and D shows resulting nanofibre nonwovens with NaCl particles (6) between the nanofibres (7) and FIG. 1 the resulting high-porosity nanofibre nonwoven with randomly oriented (A, B) and directional nanofibres (C, D).

Production Example 2: Combination with Microfibres, for Example Via Pressure Spinning Processes This variant uses fibres as porogen (6) between the nanofibres (7). This process can be carried out alternately or continuously. In the continuous process, interactions between the microfibre (6) and the electrical field must be excluded, as otherwise the depositing of the fibres (6) is too imprecise or even impossible. Material examples for pressure spinning are: Hybrid materials based on sol-gel, ethanol-soluble polymers (for example PVA).

Alternating Spinning on a Plate:

One embodiment is an alternating process by spinning on a plate (plate changes spinning units in defined time intervals) (FIG. 4A). Alternating spinning of micro- (6) and nanofibres (7) takes place in very short time intervals (20-60 s). The result is a layered structure of the high-porosity nanofibre nonwoven in the form of nanofibre layers (4) with only very little cohesion between the individual nanofibre layers (4). FIG. 5A, B shows an example of a nanofibre nonwoven by combining pressure spinning with electrospinning. Compared to the particle method, much thicker, high-porosity nanofibre nonwovens can be generated here (FIG. 5C).

According to this embodiment, a nanofibre nonwoven was produced which comprises PA6 (polyamide) as nanofibre material and titanium oxo-carboxo cluster microfibres as porogen. The porosity of such nanofibre nonwoven was 99.1% (measured by confocal reflection microscope).

Set-Up Rotating Roller:

In this set-up, the electrospinning process and the pressure spinning process can be run continuously (not mandatory; alternating is also possible). While the nanofibre spinning sources are localised from the sides, the pressure spinning process takes place from above directly onto the roller (FIG. 4B). For a better distribution of the microfibres (6), the pressure spinning head can be continuously moved back and forth in the expansion direction of the roller. If the nanofibre sources generate a similar electric field on both sides, it is also possible to balance the influence of the field on the falling microfibres (6).

Alignment of Nanofibre Sources Perpendicular to the Falling Direction of the Microfibres (6):

In this set-up, the spin/flight direction of the nanofibres (7) is oriented perpendicular to the falling direction of the microfibres (6) by placing the nanofibre sources on one side of the falling path and the grounded source on the other side (FIG. 4C). The nanofibres (7) are caught in flight by the microfibres (6) and collected on the lower collector. An advantage of this method is that the thickness of the generated nanofibre nonwoven does not influence the spinning process and the nanofibre nonwoven can thus be generated much thicker.

Set-Up Electrospinning Combined with the Unwinding of an Already Existing Microthread:

If the porogen fibre (6) has already been generated in advance, in this variant the fibre (6) can be continuously unwound from a bobbin during the spinning process and wound on the rotating roller (FIG. 4D). The bobbin moves continuously back and forth parallel to the roller and can thus control the deposit of the yarn. FIG. 5D shows an example of the combination of these microfibres (6) with the electrospun nanofibres (7). Compared to the particle method, much thicker, high-porosity nanofibre nonwovens can be generated here (FIG. 5E).

Production Example 3: Combination with 3D Printing; for Example Fused Deposition Modeling (FDM), bioprinting/bioplotting or Melt Electro Writing (MEW). These methods allow the precise positioning of the porogen (6) in the nanofibre nonwoven. Both particulate and fibrous porogens (6) can be generated via FDM. The most suitable process here is the alternating process, in which spinning and printing are alternated. This can either take place as a combined process on a rotating roller (FIG. 6A) or separately on a plate which alternates between the processes (FIG. 6B). Suitable materials are water- or ethanol-soluble thermoplastics, such as PVA. The MEW method describes a similar method that also uses an electric field to deposit the fibres as accurately as possible. In addition to FDM, the method of bioprinting/bioplotting can also be applied, which applies bio-inks made from hydrogels instead of molten plastic.

Example 2 Determining Porosities and Volume Ratios of Nanofibre Nonwovens

Example 2a Determining Porosity

Cutting out a piece of nanofibre nonwoven (with porogen (6)) and determining the macroscopic surface area (A): A=380 mm$^2$ Dissolving out the porogen (6) in water with subsequent drying of the fibres and immediate determination of the dry fibre mass: $m_{fibre}$=1.081 mg Cutting out another piece (with porogen (6)). Then dissolve out the porogen (6) with water and immediately embed the high-porosity nanofibre nonwoven (cryo, paraffin or other plastic embedding). It is important that the water is exchanged with the liquid embedding agent before it hardens. In the case of the polyamide fibres (7), the nonwoven was embedded in paraffin via an ascending alcohol series.

Generating of thin sections (in the case of paraffin embedding with a standard microtome) and transfer of the section to a microscope slide.

Removal of the embedding medium with subsequent embedding in microscopy-suitable embedding medium including cover glass Determining the thickness of the high-porosity nanofibre nonwoven (12) by microscopy: $d=200 \; \mu m$ Determining the total volume: $V_{total} = d \times A = 200 \; \mu m \times 380 \; mm^2 = 76 \; mm^3$ Determining the fibre volume $$V_{Fibres} = m_{Fibres}/density_{Polyamide6} = 1.081 \; mg/1.084 \; g/cm^3 = 0.997 \; mm^3$$

Determining porosity:

Porosity $P = (V_{total} - V_{fibres})/V_{total} \times 100 = (76-0.997) \; mm^3/76 \; mm^3 \times 100 = 98.69\%.$     (formula (A)):

Porosity $P = (Thickness_{porous \; nonwoven} \times A_{macroscopic} - m_{Fibre}/density_{Fibre \; material(Polyamide6)})/(Thickness_{porous \; nonwoven} \times A_{macroscopic}) \times 100.$     (Formula (B)):

Example 2b Determining Porosity

1. Preparation:

Dissolving out porogens from the nonwoven (for example water).

Positioning the nonwoven in a vessel with a cover slip base.

Fixing the nonwoven with a metal ring (inner diameter of the metal ring: 1 cm), wherein no mechanical stress was applied to the nanofibre nonwoven.

Filling vessel with water and positioning in confocal microscope (for example Leica LSM SP8).

2. Measurement Parameters:

Laser: 476 nm; argon—laser; basic power 25%; of which power on sample between 30 and 70%.

Detector: 476 nm±5 nm

Detector gain: 50-100

Objective: 40×

Image area (x–y): 1024×1024 pixel/290,91×290.91 μm

Image depth (z): 350-450 μm

Gradient of laser power and detector gain over the depth/thickness of the sample.

3. Evaluation:

ImageJ software

Adjustment of brightness and contrast in the complete Z-stack

Binaryisation of the complete Z-stack (black and white only)

Counting of the black and white voxels and calculation of the volume ratio (=porosity)

Example 2c Determining the Volume Ratio

To determine the volume ratio of porogen material to nanofibre material, proceed as follows:

1. drying of the nanofibre nonwoven after the spinning process
2. determining the total mass (porogen and nanofibres)
3. dissolving out the porogen
4. drying the nanofibre nonwoven
5. determining the mass of the nanofibre nonwoven
6. calculating the mass of the porogen from the total mass and the mass of the nanofibre nonwoven
7. calculating the volumes of porogen material and nanofibre material and calculating their ratio.

Example 3

Application Example Matrix Stromal Tissue

Connective tissue is one of the most important components of organs or organ models. The nanofibre nonwoven disclosed here is suitable for a variety of tissues such as: Heart, respiratory tract, intestine, bone, cartilage, kidney, urogenital tract, liver or vessels. Tissue-specific properties can be generated by using fibroblasts from the respective tissue and then attaching the stromal matrix to the respective epithelial tissue. As an example, the structure of a skin model is described in which the dermis is based on the high-porosity nanofibre nonwoven.

In this example, nanofibre nonwovens are used, which were produced according to the manufacturing example 1 "Set-up rotating roller" (see example 1). The mesh size and number can be taken from FIG. 12.

First, the dry nanofibre nonwoven (with porogen (6)) is cut to the desired size (for example 2.5×2.5 cm). Then the porogen (6) is dissolved out in a suitable solvent (for example water) and the nanofibre nonwoven is clamped in the culture device. A cell crown or a Transwell® insert can be used for this purpose, for example. Depending on the desired thickness of the dermal part, for example, 2 or 4 nanofibre nonwovens with thicknesses of 200 μm can be stacked on top of each other (correspondingly less for thicker nanofibre nonwovens). Human fibroblasts (40000 cells/cm²) are then seeded on the nanofibre nonwoven. After 2-4 weeks of culture, the nanofibre nonwoven is completely colonised and matrix proteins are synthesised within the pores (5) and meshes (8). After this biologisation of the nanofibre nonwoven, human keratinocytes (600000 cells/cm²) are seeded and cultivated for 3 weeks under airlift conditions. During this time, the epidermis forms on the nanofibre-based connective tissue and results in a skin model of approx. 1 cm² based on synthetic nanofibres (FIG. 7A). The application of the biologised nanofibre nonwoven results in a fully formed epidermis with all relevant layers and a thickness of 150-200 μm (FIG. 7B). IF (immunofluorescence) staining against vimentin shows a homogeneous distribution of fibroblasts in the stromal tissue of the fibre nonwoven (FIG. 7C). Furthermore, it can be seen in the close-up that the cells are mainly located on the nanofibres (7). In contrast, when looking at the collagen I distribution, this matrix protein is located both on the nanofibres (7) and in the pores (5) (FIG. 7D). IF staining against differentiation-specific markers of the epidermis confirms its mature status (FIG. 7E) and the formation of a basement membrane (FIG. 7F).

Application Example Attachment of Stromal to High-Porosity Tissues Such as Adipose Tissue Often organs do not consist of only one tissue type, but stromal tissues alternate with high-porosity tissues and are in continuous exchange with each other. The nanofibre nonwoven described here makes it possible to attach both types, which is shown below in the connection of the dermis with the subcutis.

In the skin, the dermis describes only the uppermost connective tissue part of this organ. The next layer down is the subcutis, which is mainly composed of adipose tissue. Adipogenic differentiation of mesenchymal stromal cells (MSCs) can produce the cellular portion of adipose tissue. Due to the strong increase in volume, only very porous structures are suitable as scaffolds. Furthermore, MSCs cannot be combined with keratinocytes in a model from the outset, as the different media have a mutually negative effect on the differentiation of the various cells. The advantage of these high-porosity nanofibre nonwovens is that both cell types colonise the nanofibre nonwoven separately and subsequently differentiate separately.

Finally, the nanofibre nonwovens can be assembled and the tissue can mature over a certain time frame.

In detail, the production of the upper part (dermis—epidermis is analogous to the previous text section). To generate the adipose tissue, MSCs (100000 cells/cm$^2$) are seeded on the fibre nonwoven and initially cultivated for 2 weeks. Subsequently, adipogenic differentiation takes place for another 2 weeks. After this time, this differentiation is so far advanced that a change from adipogenic differentiation medium to keratinocyte medium has no negative effect on these cells. Therefore, the adipogenic tissue can now be attached to the skin model from below and mature together for 2-3 weeks. FIG. 8A, B shows the resulting 3-layer skin model based on the high-porosity nanofibre nonwoven. In the HE stain (FIG. 8A), the fat droplets are located at the positions of the holes because the fat was washed out by the embedding process (paraffin). By using cryoembedding, the lipids are obtained and can be stained. For example, using the fluorescent dye Nile Red (FIG. 8B) or the red dye Oil Red (FIG. 8C). Staining with oil red can also make the nanometre-scale lipid droplets in the uppermost layer of the epidermis visible (FIG. 8D).

The invention claimed is:

1. A nanofibre nonwoven comprising a network of nanofibres (7) composed of at least one nanofibre material and enclosing pores (5), produced by a method comprising the method steps:
   a) providing at least one nanofibre material and at least one porogen material suitable for formation of at least one porogen,
   b) electrospinning the at least one nanofibre material while introducing at least one porogen (6) formed from the at least one porogen material and the porogen having a diameter of 30 to 1000 μm, so that the volume ratio of porogen material to nanofibre material in the electrospun nanofibre nonwoven obtained after completion of this method step is 40:99 to 60:1 based on a total volume of fibres and porogens of a nanofibre nonwoven), wherein the at least one nanofibre material is present in a form of nanofibre layers, wherein a pore is space enclosed by nanofibre layers which can be filled by porogens, cells or fluids, wherein the pores spatially separate the individual nanofibre layers from each other, wherein a nanofibre layer is a layer of nanofibres arranged above and/or next to one another, wherein, insofar as the porogen is provided in method step a) as a ready-formed porogen, in method step b) an introducing of the porogen and the electrospinning of the nanofibre material is carried out alternately, or insofar the porogen material provided in method step a) is a material suitable for forming at least one fibrous porogen in method step b) at least one fibrous porogen is formed from the porogen material before or during its introduction into the electrospun nanofibre material; and
   c) obtaining the nanofibre nonwoven comprising at least one porogen (6).

2. The nanofibre nonwoven according to claim 1, wherein the method further comprises the following method steps:
   d) incubating the nanofibre nonwoven obtained in method step c) comprising at least one porogen (6) in at least one solvent to at least partially remove the at least one porogen from the nanofibre nonwoven; and
   e) obtaining a nanofibre nonwoven.

3. The nanofibre nonwoven according to claim 1, wherein the porogen material provided in method step a) is particulate or fibrous, has a diameter of 30 to 1000 μm and is provided in method step a) as the formed porogen (6).

4. The nanofibre nonwoven according to claim 1, wherein the porogen material provided in method step a) is a material suitable for forming at least one fibrous porogen (6) and in method step b) at least one fibrous porogen is formed from the porogen material before or during its introduction into the electrospun nanofibre material.

5. The nanofibre nonwoven according to claim 1, comprising a network of nanofibres (7) composed of at least one nanofibre material and enclosing pores (5), wherein the porosity of the nanofibre nonwoven is 90.0 to 99.9 vol. %, in particular 98.5 to 99.9 vol. % (in each case based on the total volume of the nanofibre nonwoven).

6. The nanofibre nonwoven according to claim 1, wherein at least one liquid is present in the nanofibre nonwoven, in particular 90.0 to 99.9 vol. % of liquid (based on the total volume of the nanofibre nonwoven).

7. The nanofibre nonwoven according to claim 1, wherein the pores (5) in the nanofibre nonwoven are distributed homogeneously or in a hierarchically structured manner.

8. The nanofibre nonwoven according to claim 1, wherein the nanofibre nonwoven additionally comprises porogens (6).

9. The nanofibre nonwoven according to claim 8, wherein the porogens (6) are particulate or fibrous.

10. The nanofibre nonwoven according to claim 8, wherein the porogens (6) have a diameter of 30 to 1000 μm.

11. The nanofibre nonwoven according to claim 1, comprising a network of nanofibres (7) composed of at least one nanofibre material and enclosing pores (5), wherein the nanofibre nonwoven has at least 90.0 to 99.9 vol. % of liquid (based on the total volume of the nanofibre nonwoven).

12. A method for producing a nanofibre nonwoven comprising a network of nanofibres (7) composed of at least one nanofibre material and enclosing pores (5), comprising the following method steps:
   a) providing at least one nanofibre material and at least one porogen material suitable for formation of at least one porogen,
   b) electrospinning the at least one nanofibre material while introducing at least one porogen (6) formed from the at least one porogen material and the porogen having a diameter of 30 to 1000 μm, so that the volume ratio of porogen material to nanofibre material in the electrospun nanofibre nonwoven obtained after completion of this method step is 40:9940 to 99 to 60:160 to 1 (in each case volume based on a total volume of, i.e. fibres and porogens of a nanofibre nonwoven), wherein the at least one nanofibre material is present in a form of nanofibre layers, wherein a pore is space enclosed by nanofibre layers which can be filled by porogens, cells or fluids, wherein the pores spatially separate the individual nanofibre layers from each other, wherein a nanofibre layer is a layer of nanofibres arranged above and/or next to one another, wherein, insofar as the porogen is provided in method step a) as a ready-formed porogen, in method step b) an introducing of the porogen and the electrospinning of the nanofibre material is carried out alternately, or insofar the porogen material provided in method step a) is a material suitable for forming at least one fibrous porogen in method step b) at least one fibrous porogen is formed from the porogen material before or during its introduction into the electrospun nanofibre material;

c) obtaining the nanofibre nonwoven comprising at least one porogen (6), in particular having a porosity of 90.0 to 99.9 vol. %, in particular 98.5 to 99.9 vol. % (in each case based on the total volume of the nanofibre non-woven), preferably having a porosity of 90.0 to 99.9%, in particular 98.5 to 99.9 vol. % (in each case based on the total volume of the nanofibre nonwoven) and meshes (8) with a width of 10 to 200 μm2 (measured in water without porogen (6)).

13. The method for producing a nanofibre nonwoven according to claim 12, further comprising the method steps:

d) incubating the nanofibre nonwoven obtained in process step c) comprising at least one porogen (6) in at least one solvent to at least partially remove the at least one porogen from the nanofibre nonwoven; and e) obtaining a nanofibre nonwoven resulting from the incubation.

14. The method for producing a nanofibre nonwoven according to claim 12, wherein the porogen material provided in method step a) is particulate or fibrous, has a diameter of 30 to 1000 μm and is provided in method step a) as formed porogen (6).

15. The method for producing a nanofibre nonwoven according to claim 12, wherein the porogen material provided in method step a) is a material suitable for forming at least one fibrous porogen (6), and in method step b) at least one fibrous porogen is formed from the porogen material before or during its introduction into the electrospun nano-fibre material.

16. A method for cultivation or differentiation of cells, comprising culturing cells in the nanofibre nonwoven according to claim 1.

17. An artificial tissue comprising a nanofibre nonwoven according to claim 1, and at least one cell of at least one cell type.

18. The artificial tissue according to claim 17, wherein the artificial tissue comprises 1 to 50 wt. % nanofibre nonwoven and 50 to 99 wt. % cells, in particular 80 to 99 wt. %, and, optionally, extracellular matrix (in each case based on the total weight of the artificial tissue).

19. The artificial tissue according to claim 17, wherein the at least one porogen (6) present in the nanofibre nonwoven has been at least partially removed from the nanofibre nonwoven prior to colonization with at least one cell of at least one cell type.

20. A method for producing an artificial tissue according to claim 17, comprising the following method steps:

x) providing a cell of at least one cell type, a culture medium and at least one nanofibre nonwoven according to any one of claims 1 to 11 or producible by a method according to any one of claims 12, x2) optionally removing at least a part of an optionally present at least one porogen (6), x3) cultivating the at least one nanofibre nonwoven with the at least one cell of the at least one cell type in the culture medium, and x4) obtaining an artificial tissue comprising the at least one cell arranged on or in the at least one nanofibre nonwoven.

21. The method according to claim 20, wherein during or after the cultivation according to method step x3) the nonwoven is cultivated in a method step x31) with at least one cell of at least one further cell type, in particular a cell type different from the cell type provided in method step x1).

22. The method according to claim 20, wherein during or after the cultivation according to method step x3) or x31) further nanofibre nonwovens, preferably colonized with at least one cell of an identical or different cell type, are stacked on the nanofibre nonwoven obtained in x3) or x31).

\*  \*  \*  \*  \*